United States Patent
Gouko et al.

(10) Patent No.: US 10,054,504 B2
(45) Date of Patent: Aug. 21, 2018

(54) APPARATUS FOR DETECTING CHANGES IN A LOAD APPLIED THERE-TO

(71) Applicant: DENSO CORPORATION, Kariya, Aichi-pref. (JP)

(72) Inventors: Norio Gouko, Kariya (JP); Toshihisa Taniguchi, Kariya (JP); Atusi Sakaida, Kariya (JP); Keiji Okamoto, Kariya (JP); Yoshihiko Shiraishi, Kariya (JP); Masahiro Asano, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/619,610

(22) Filed: Jun. 12, 2017

(65) Prior Publication Data

US 2017/0356818 A1 Dec. 14, 2017

(30) Foreign Application Priority Data

Jun. 14, 2016 (JP) .................. 2016-118259

(51) Int. Cl.
| | |
|---|---|
| *G01B 7/16* | (2006.01) |
| *G01L 5/00* | (2006.01) |
| *G01L 5/04* | (2006.01) |
| *G01G 3/13* | (2006.01) |
| *G01L 5/10* | (2006.01) |

(Continued)

(52) U.S. Cl.
CPC .............. *G01L 5/0028* (2013.01); *G01G 3/13* (2013.01); *G01K 17/08* (2013.01); *G01L 5/04* (2013.01); *G01L 5/047* (2013.01); *G01L 5/10* (2013.01); *G01N 25/20* (2013.01)

(58) Field of Classification Search
CPC ......... G01L 5/0028; G01L 5/04; G01L 5/047; G01L 5/10; G01G 3/13; G01K 17/08; G01N 25/20
USPC ........................................... 73/763
See application file for complete search history.

(56) References Cited

U.S. PATENT DOCUMENTS

| | | | | |
|---|---|---|---|---|
| 5,903,380 A | * | 5/1999 | Motamedi ............. | B81B 3/0035 359/202.1 |
| 6,080,988 A | * | 6/2000 | Ishizuya ................... | G01J 5/06 250/330 |

(Continued)

FOREIGN PATENT DOCUMENTS

JP 2002-286538 A 10/2002

*Primary Examiner* — Max Noori
(74) *Attorney, Agent, or Firm* — Harness, Dickey & Pierce, P.L.C.

(57) ABSTRACT

A load change detection apparatus is provided with a base member, an elastic member, a first plate, a fixing member and heat flow sensors. The elastic member deforms according to a changed load applied to the elastic member, received by the receiving member. The first plate supports a surface of the elastic member on a side of the base member. The fixing member fixes the lower plate and the elastic member to the base member. The heat flow sensors, provided between the base member and the lower plate, output signals according to heat flowing between the lower plate and the base member. The heat flows due to heat generated or heat absorbed when the elastic member changes the elasticity shape thereof. Stress occurring when the elastic member deforms, is shut off by the first plate, thus direct transmission of the stress to the heat flow sensors is avoided.

20 Claims, 12 Drawing Sheets

(51) Int. Cl.
*G01K 17/08* (2006.01)
*G01N 25/20* (2006.01)

(56) References Cited

U.S. PATENT DOCUMENTS

| | | | |
|---|---|---|---|
| 6,598,960 B1* | 7/2003 | Cabal | B41J 2/14427 |
| | | | 347/56 |
| 9,239,431 B1* | 1/2016 | Rakich | G02B 6/12007 |
| 2007/0189920 A1* | 8/2007 | Gimzewski | G01K 1/16 |
| | | | 422/51 |
| 2012/0090387 A1* | 4/2012 | Djakov | G01N 11/16 |
| | | | 73/61.76 |

* cited by examiner

APPARATUS FOR DETECTING CHANGES IN A LOAD APPLIED THERE-TO

CROSS-REFERENCE TO RELATED APPLICATION

The application is based on and claims the benefit of priority from earlier Japanese Patent Application No. 2016-118259, filed on Jun. 14, 2016, the description of which is incorporated herein by reference.

BACKGROUND OF THE INVENTION

Technical Field

The present disclosure relates to an apparatus for detecting changes in a load applied received by a receiving member and more specifically, relates to an elastic member which deforms according to an applied load.

Related Art

Conventionally, detectors which detect a load applied from a receiving member are known. JP2002-286538A discloses a load detector as a load cell provided with a strain body which deforms due to an applied load received by the receiving member, and a strain gauge as an electric resistor, mounted on a surface of the strain body. The strain body which deforms according to a size of the load applied by the receiving member and the strain gauge expands or compresses, which changes a resistance value of the strain gauge. As a result, the load cell can detect the size of the load applied to the strain body, received by the receiving member, by deformation of the strain element to an electric signal.

Incidentally, load cells are generally used to detect a static load applied to a strain body which is received by the receiving member. If an impact is applied, in addition to the load received by the receiving member, to the strain body, which causes further strain or excessive stress, for example, the strain gauge may be ripped off from a surface of the strain body or the strain gauge itself broken, for example, which may in turn damage the load cell. It is thus desirable to develop a load detecting device in which such damage due to the applied load received by the receiving member is prevented from occurring.

Additionally, although it is possible to detect the size of an applied load received by receiving member, it can be difficult to directly detect a change of the load. It is thus also desirable to develop a device which can detect a load change applied from receiving member.

SUMMARY

It is an object of the present disclosure to provide an apparatus which has a capability of detecting changes in a load applied to a receiving member, which can also avoid malfunction occurring in the apparatus due to the change of the load applied.

In order to satisfy an object of a first mode of the present disclosure, an apparatus for detecting changes in a load applied thereto is provided with a base member, an elastic member, a first plate, a fixing member and heat flow sensors. The elastic member is provided to change shape thereof according to an applied load change received by a receiving member. The first plate supports a surface on a side which is a side of the base member. The fixing member is used to fix the first plate and the elastic member to the base member.

The heat flow sensors provided between the base member and the first plate, output signals corresponding to heat flow from heat that is generated or absorbed when the elastic member deforms, which flows between the first plate and the base member.

According to the configuration described, the elastic member changes shape, that is, elastically deforms, according to the load change applied from a receiving member, and heat flows between the first plate and the base member according to the heat generated or absorbed at the elastic member. The heat flow sensors provided between the first plate and the base member output signals corresponding to a size of a changed shape of the elastic member, which changes shape according to the load change applied to the elastic member, received by the receiving member. The load change detection apparatus can thus detect a size of the load change applied.

Stress occurring when the elastic member changes shape thereof is blocked by the first plate, thus the stress is not directly transmitted to the heat flow sensors. As a result, damage to the heat flow sensors, for example, from a significant impact, is avoided even when the elastic member receives such an impact received by the receiving member, for example. Furthermore, the load change detection apparatus can prevent malfunction of the heat flow sensors caused by an applied load change received by the receiving member.

It is noted that symbols are to exemplify a corresponding means in embodiments described hereinafter.

PREFERRED EMBODIMENTS

The preferred embodiments for the present disclosure will now be described based on the accompanying drawings. It is noted that same symbols are used to describe the same elements in each of the embodiments.

First Embodiment

The first embodiment will now be described with reference to the figures. An apparatus for detecting changes of load applied thereto will also be referred to as 'a load change detection apparatus' hereon. The load change detection apparatus according to the first embodiment detects a change of a load applied from a receiving member.

Figure 1:
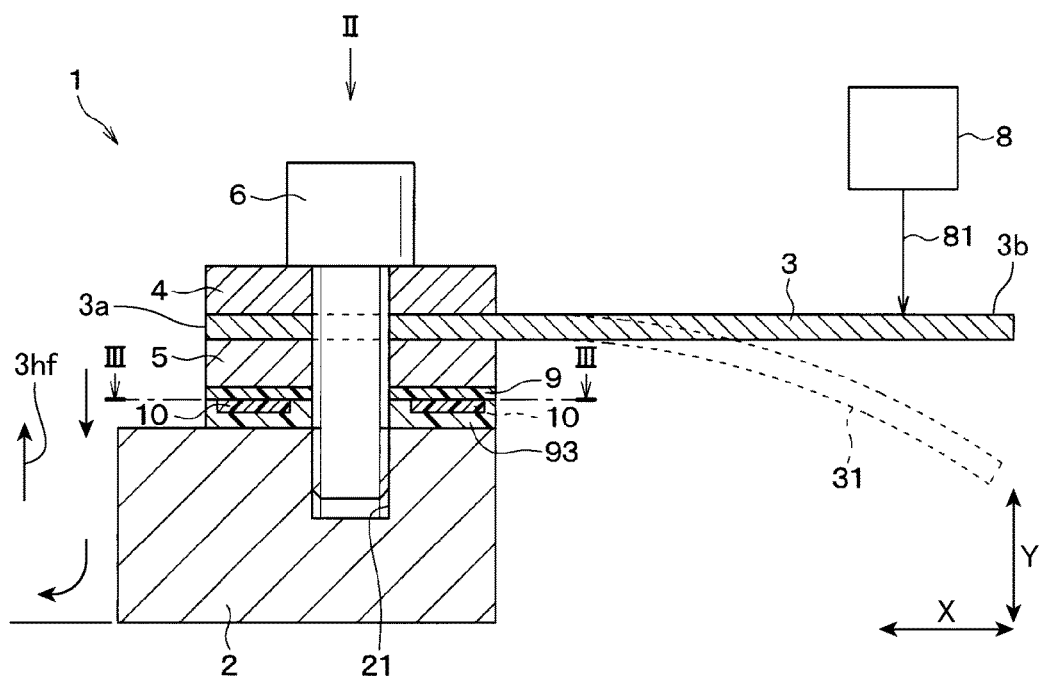
FIG. 1 is cross sectional configuration showing a load change detection apparatus according to the a first embodiment of the present disclosure.
Figure 2:
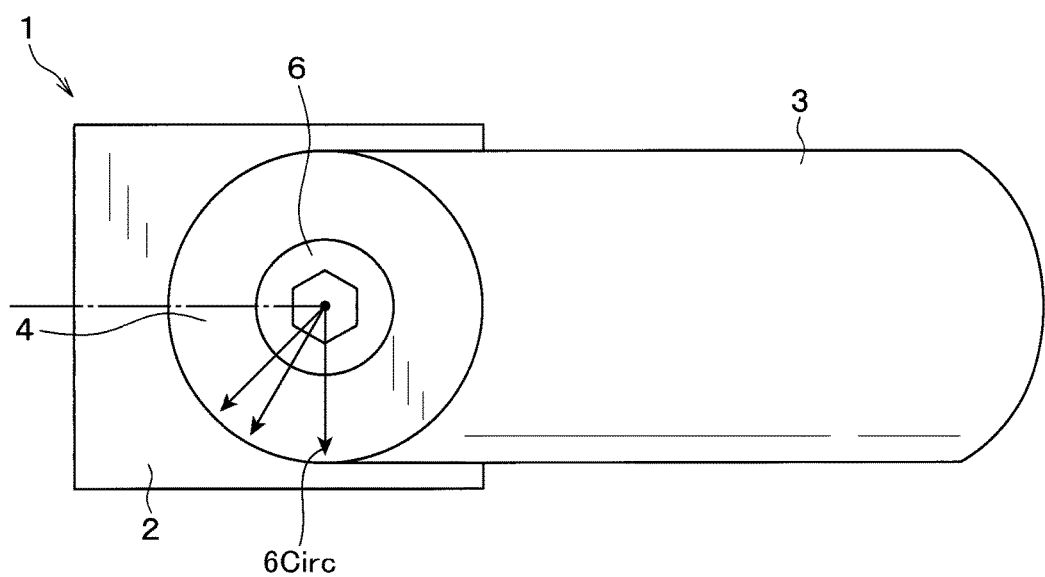
FIG. 2 is a plan view in a direction of a line II shown in FIG. 1.
Figure 3:
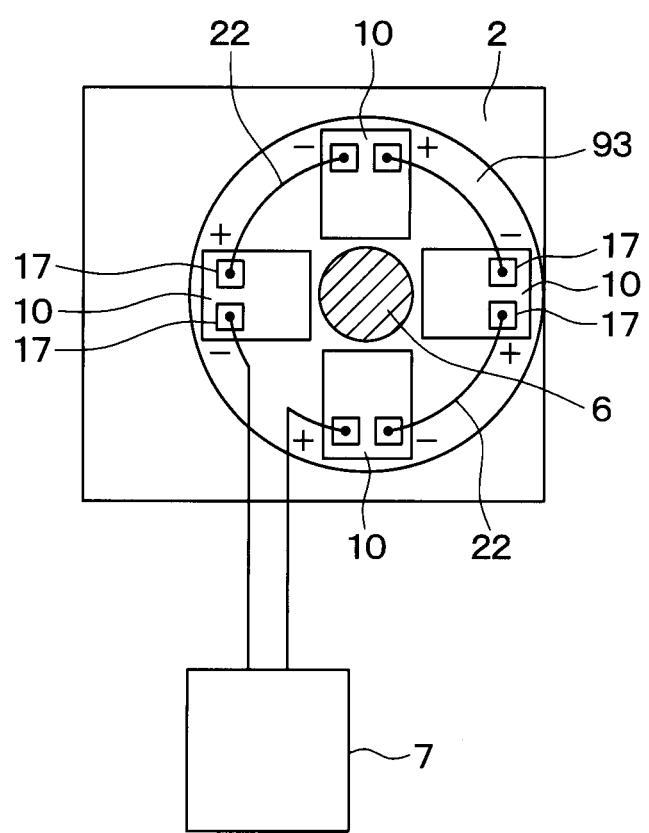
FIG. 3 is a cross sectional view taken across a line III-III shown in FIG. 1.

As shown in FIG. 1 to FIG. 3, the load change detection apparatus 1 is provided with a base member 2, an elastic member 3, an upper plate 4 (second plate), a lower plate 5 (first plate), a screw member 6, heat flow sensors 10 and a detector 7, for example. It is noted that, the detector 7 is schematically shown in FIG. 3 only, and omitted from FIG. 1 and FIG. 2.

The base member 2 is formed from metal, for example, and has a predetermined thermal capacity. A housing used in various devices is an example of the kind of configuration can be used for the base member 2, that is, any formation maybe employed as the base member 2, as long as it functions as a base of the load change detection apparatus 1.

The base member 2 is provided with a screw hole 21, to receive the screw member 6 which is the fixing member. A circumferential direction 6 Circ of the screw member 6 is indicated in FIG. 2.

The elastic member 3 is formed from metal, for example, and is fixed to the base member 2 by the screw member 6, with the upper plate 4 and the lower plate 5 sandwiched between. The elastic member 3, the upper plate 4, and lower plate 5 are each provided with a hole in a center thereof, in a plate thickness direction. The screw member 6 passes through each of the respective holes, and is screwed in the screw hole 21 provided on the base member 2. As a result, the upper plate 4, the elastic member 3 and the lower plate 5 are fixed to the base member 2 by the screw member 6.

The elastic member 3 is a cantilever beam member which extends from the lower plate 5 to an external side thereof. An end 3a of the elastic member 3 is attached to the base member 3 as described above, and a second end 3b is a free end which is unattached. When the receiving member 8 moves in a direction of an arrow 81, shown in FIG. 1, and applies a load to the second end 3b which is the free end, the elastic member 3 bends in a manner indicated with a broken line 31 in FIG. 1. A bending degree of the elastic member 3 corresponds to a size of the load applied received by the receiving member 8. Also, when the applied load received by the receiving member 8 is removed therefrom, the elastic member 3 returns to its original position. That is, the elastic member 3 deforms in accordance to a load change applied to the receiving member 8.

Both the upper plate 4 and the lower plate 5 are formed in a plate shape from a material with high thermal conductivity, such as metal, for example. The upper plate 4 supports a surface of the elastic member 3, on a side which opposes a side of the base member 2, and the lower plate 5 supports a surface of the elastic member 3 on a side of the base member 2.

As shown in FIG. 1, the heat flow sensors 10 are provided with an insulating sheet 9 and a buffer member 93 sandwiched between the lower plate 5 and the base member 2, so that the insulating sheet 9 and the buffer member 93 are disposed respectively, on sides of the lower plate 5 and the base member 2.

The insulating sheet 9 is formed from a resin, such as polyamide, for example. The insulator 9 block electrical conduction between a terminal 17 of the heat flow sensors 10 and the upper plate 4.

The buffer 93 is formed from a fluorocarbon polymer such as polytetrafluoroethylene, for example. The buffer member 93 absorbs unevenness due to the terminal 17 provided on a surface of the heat flow sensors 10, or due to wiring 22 connected to the terminal 17, or to a solder which connects the terminal 17 and the wiring 22. Incidentally, either an adhesive agent can be applied or a double sided tape may adhered between the buffer member 93 and the base member 2, and between the insulating sheet 9 and the lower plate 5. The buffer member 93 may be provided between the heat flow sensor 10 and the upper plate 4, alternatively to the insulating sheet 9.

The heat flow sensors 10 output signals according to heat flowing in a thickness direction thereof. That is, with reference to FIG. 1, the heat flow sensors 10, output the signals according to heat flowing between the lower plate 5 and the base member 2, indicated with arrows 3hf. As shown in FIG. 3, for example, four heat flow sensors 10 are provided around a central axis of the elastic member 3. The four heat flow sensors 10 are each electrically connected in series by the wiring 22 connected to each of the respective terminals 17. An output of signals from the four heat flow sensors 10 is input to the detector 7.

The configuration of the heat flow sensor 10 will now be described.

Figure 4:
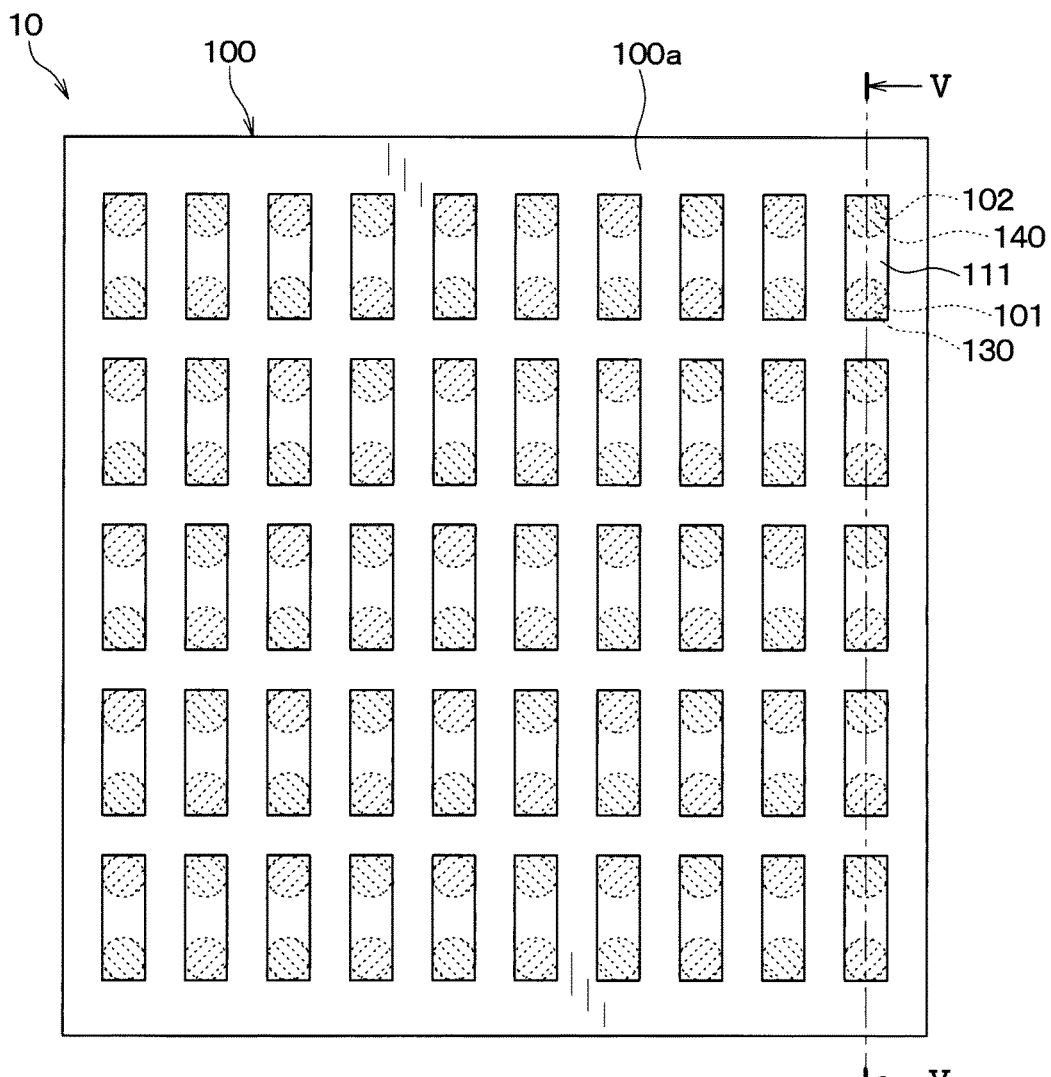
FIG. 4 is a plan view of heat flow sensors shown in FIG. 3.
Figure 5:
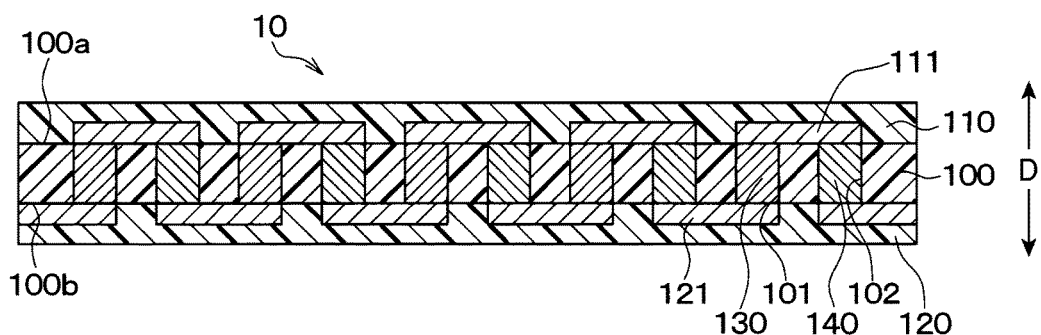
FIG. 5 is a cross sectional view across a line V-V shown in FIG. 4.

As shown in FIG. 4 and FIG. 5, an insulator 100, a surface protection member 110 and a bottom side protection member 120 are integrated in the heat flow sensor 10. A first and a second interlayer connector 130 and 140 respectively, are configured to be alternately connected in series. It is noted that, the surface protection member 110 is omitted from FIG. 4. The insulator member 100, the surface protection member 120 and the bottom side protection member are film members, formed from resin materials having flexibility, for example, thermoplastic resin. A plurality of first and second via holes 101 and 102, pierced through in a thickness direction thereof are formed on the insulator 100.

The thickness direction of the heat flow sensors is indicated with arrows D, in FIG. 5. The first and second interlayer connectors 130 and 140, each configured of a different thermal material, such as, a different metal or semiconductor, are embedded in the first and second via holes 101 and 102. The insulator 100 is provided with a surface side 100a and a bottom side 100b. One connection member of the first and second interlayer connectors 130 and 140 is configured by a surface conductor pattern 111 disposed in the surface 100a of the insulator 100.

A second connection member of the first and second interlayer connectors 130 and 140 is configured by a bottom side conductor pattern 121 disposed on the bottom side of the insulator 100b.

A temperature difference occurs between the first connection member and second connection member of the first and second interlayer connectors 130 and 140, when the heat flow passes through the heat flow sensors 10 in the thickness direction D thereof. As a result, thermal electromotive force is generated at the first and second interlayer connectors 130 and 140, by the Seebeck Effect. The heat flow sensors 10, output the thermal electromotive force, for example, as a sensor signal of a voltage.

As shown in FIG. 1, the elastic member 3 bends in the direction indicated with the broken line 31 in FIG. 1, according to an applied load change received by the receiving member 8, in the direction shown with an arrow 81. In turn, the elastic member 3 generates heat which corresponds to the bending degree thereof. The heat generated from the elastic member 3 flows to the base member 2, along a route via the lower plate 5, the insulating sheet 9, the heat flow sensor 10 and the buffer member 93. The heat flow sensor 10 provided on the route in which the heat flows, outputs a signal which corresponds to heat flowing between the lower plate 5 and the base member 2. It is noted that, the heat generated from the elastic member 3 in part, includes heat flowing to the base member 2 via the upper plate 4 and the screw member 6.

Once the heat flow passes through the four heat flow sensors 10 in the thickness direction thereof, signals output from the four heat flow sensors 10 are input into the detector 7. The detector 7 is configured of a microcomputer and other peripheral devices, for example. The detector 7 can detect whether a load change is applied to the elastic member 3, received by the receiving member 8, and the size of the load change, based on the signals output from the four heat flow sensors 10.

Incidentally, stress occurring when the elastic member 3 bends, is blocked by the lower plate 5, and is not directly transmitted to the heat flow sensors 10. As a result, even if an impact received by the receiving member 8 reaches the elastic member 3, damage to the heat flow sensors 10 from the impact can be prevented.

The load change detection apparatus 1 according to the first embodiment provides the following effect.

Effect 1

In the first embodiment, heat flows between the lower plate 5 and the base member 2 when the elastic member 3 elastically deforms according to an applied load change received by the receiving member 8. The heat flow sensors 10, provided between the lower plate 5 and the base member 2, output signals corresponding to the heat flow. More specifically, the signals output from the heat flow sensors 10 correspond to a size of the change of the elastic member, which changes shape according to a load change applied to the elastic member received by the receiving member 8. The load change detection apparatus 1 can thus detect whether a load change is applied to the elastic member, which is received by the receiving member 8, in addition to the size of the load change.

The heat flow sensors 10 do not directly detect by measuring a size of deformation of the elastic member 3 such as in a strain gauge. In fact, the heat flow sensors 10 detect the heat flow generated from the elastic member 3. Direct transmission of stress from the elastic member 3 to the heat flow sensors 10 is thus blocked by the lower plate 5. As a result, the load change detection apparatus 1 can avoid a failure of the heat flow sensors 10 caused by an applied load change received by the receiving member 8.

Effect 2

The load change detection apparatus 1 according to the first embodiment is provided with the buffer member 93 disposed at least between the heat flow sensors 10 and the lower plate 5, or between the heat flow sensors 10 and the buffer member 93.

In the configuration described, when unevenness occurs on the surface of the heat flow sensors 10, for example, the lower plate 5, the heat flow sensor 10, the base member 2 and the buffer member 93 are closely adhered to each other, since the buffer member 93 absorbs the unevenness thereof. The load change detection apparatus 1 can thus increase the output of the heat flow sensors 10 by enhancing the heat flow between each of the constituting members.

The elastic member 3 in the first embodiment is the cantilever beam member which extends from the lower plate 5 to the external side thereof.

According to the configuration, the cantilever beam member changes shape and generates or absorbs heat according to an applied load change received by the receiving member 8. In turn, the heat flow sensors 10 output signals corresponding to the heat flowing between the lower plate 5 and the base member 2, when the cantilever beam member generates or absorbs the heat. The load change detection apparatus 1 can thus detect the size of the load change applied to the elastic member 3, which is received by the receiving member 8.

Embodiment 2

The second embodiment of the present disclosure will now be described. Configuring elements of the second embodiment are the same as the configuring elements described in the first embodiment, with the exception of the heat flow sensors 10. That is, the heat flow sensor 10 in the second embodiment has a different configuration from the first embodiment. Thus only parts which are different from the first embodiment will be described hereinafter.

Figure 6:
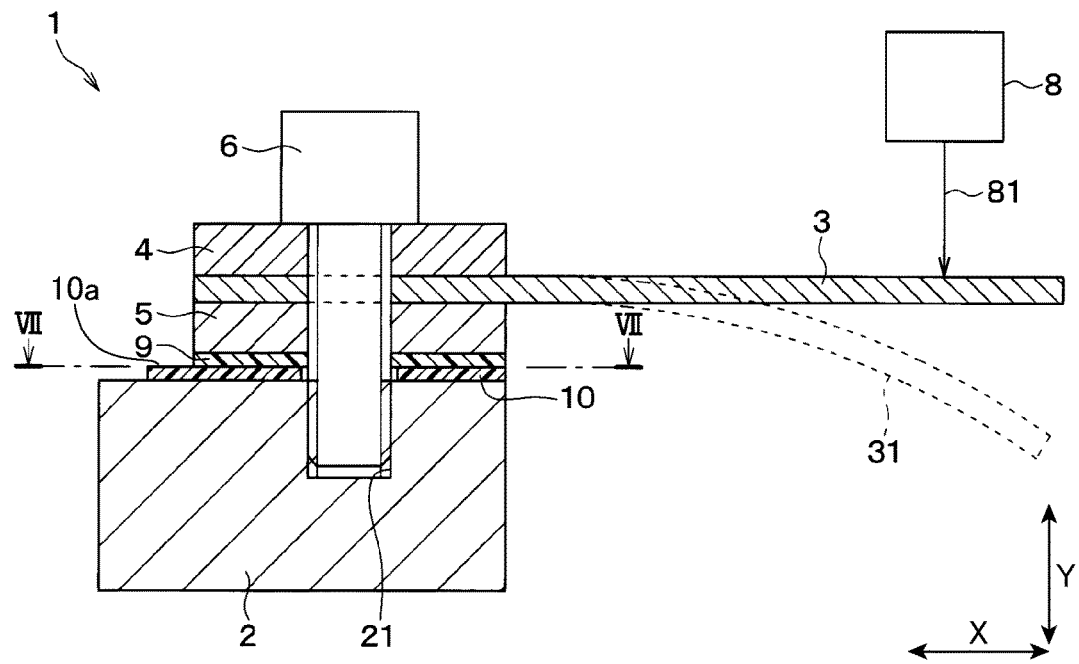
FIG. 6 is a cross sectional view showing a load change detection apparatus according to a second embodiment.
Figure 7:
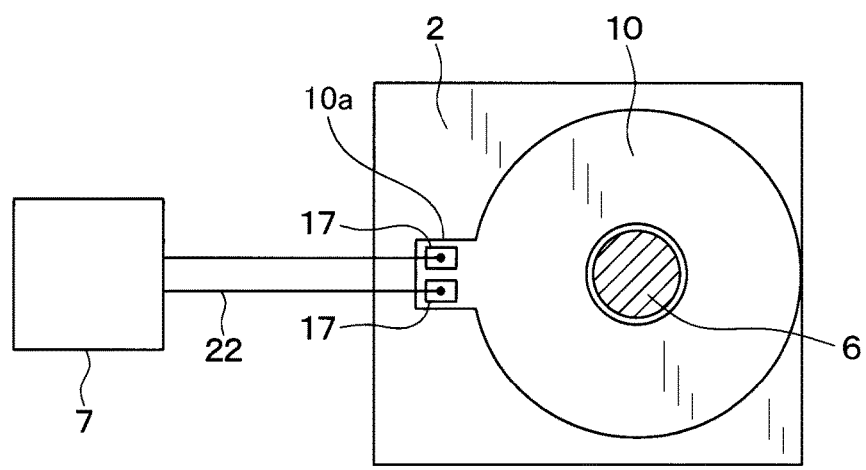
FIG. 7 is a cross sectional view across a line VII-VII shown in FIG. 6.

As shown in Hg. 6 and FIG. 7, the heat flow sensor 10 in the second embodiment is a circular shape formed around the central axis of the elastic member 3. The heat flow sensors 10 also have a section in which the terminals 17 are mounted, and projected in a radial direction to an external side from a section 10a of an outer periphery thereof. The section 10a, is projected towards the external side, with reference to the lower plate 5, as indicated in FIG. 6. As a result, in the second embodiment, unevenness of surface in which the lower plate 5 and the base member 2 are sandwiched therebetween is reduced, with respect to the heat flow sensors 10. Furthermore, the buffer member 93 provided between the heat flow sensors 10 and the base member 2 in the first embodiment may be omitted from the second embodiment.

As with the first embodiment, the heat flow sensor 10 in the second embodiment also outputs signals according to heat flowing between the lower plate 5 and the base member 2, which corresponds to the heat generated by the elastic member 3. The load change detection apparatus 1 can thus detect the size of a load change applied to the elastic member 3 received by the receiving member 8.

Additionally according to the second embodiment, by forming the heat flow sensor 10 in a circular shape to be disposed circumferentially around the screw member 6, which is used to fix the elastic member 3, an area in which the heat flow sensor 10 is mounted on the route of the heat flowing between the lower plate 5 and the base member 2 can be increased. As a result, the output of the heat flow sensors 10 can be enhanced by increasing a number of the first and second interlayer connectors 130 and 140 provided on the heat flow sensors 10.

Embodiment 3

The third embodiment of the present disclosure will now be described.

Figure 8:
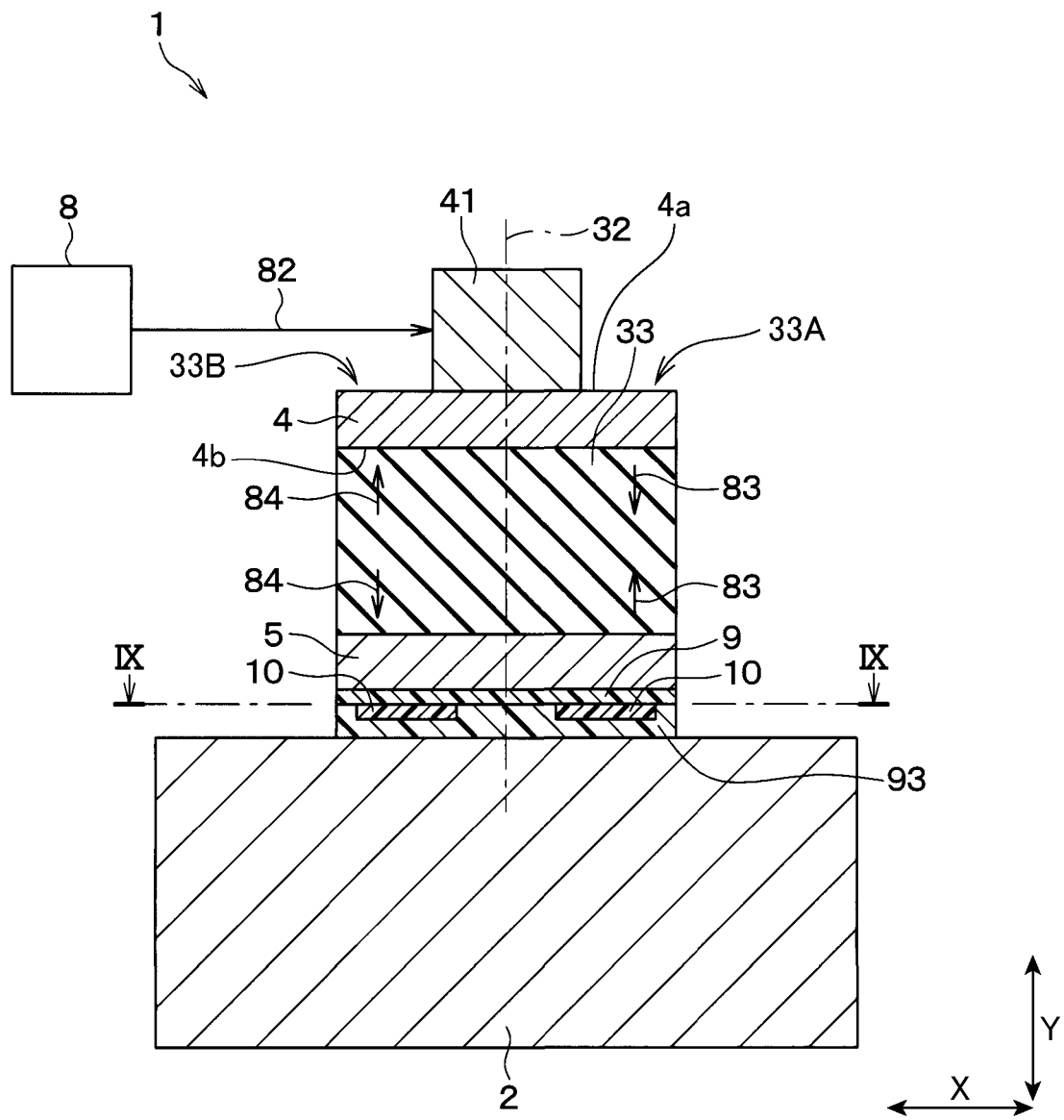
FIG. 8 is a cross sectional view showing a load change detection apparatus according to a third embodiment.
Figure 9:
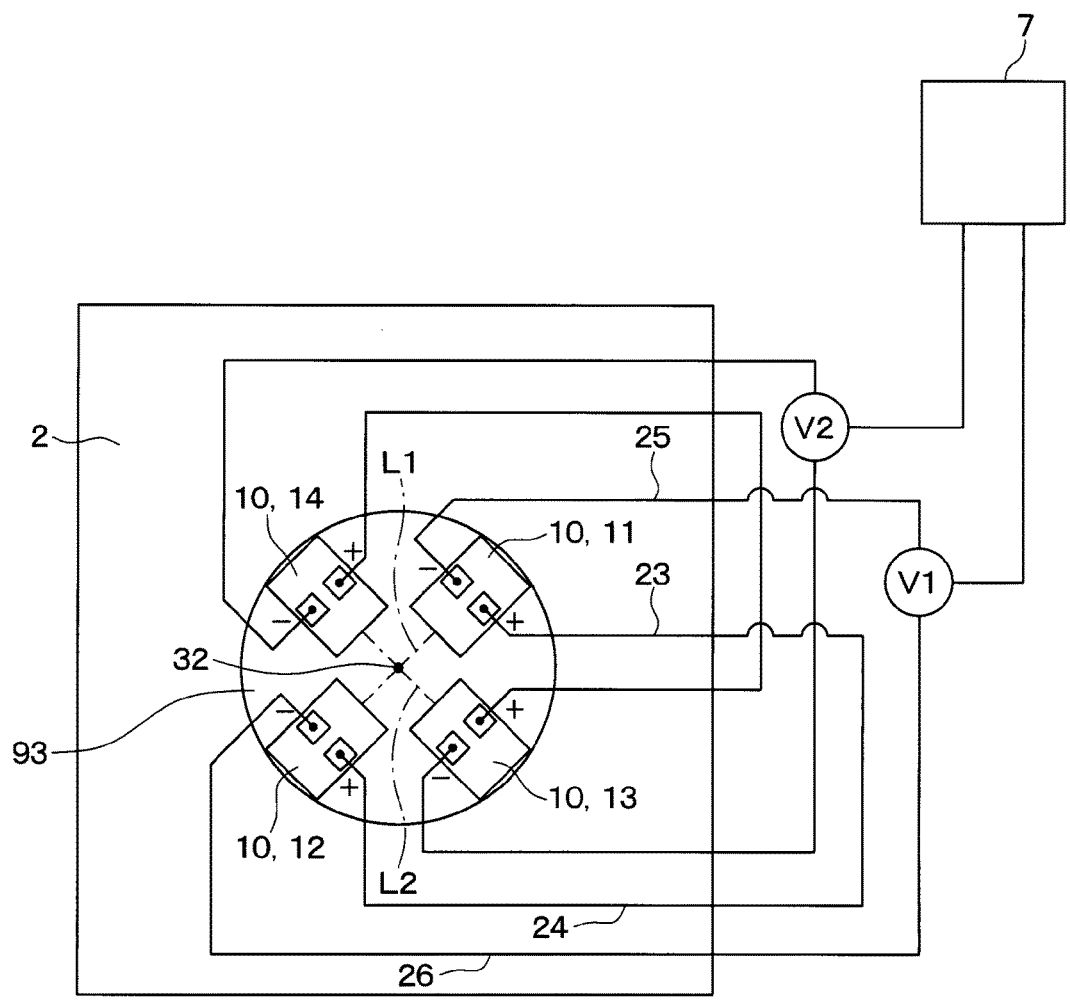
FIG. 9 is a cross sectional view across a line IX-IX shown in FIG. 8.

As shown in FIG. 8 and FIG. 9, in the third embodiment, the elastic member 33 is made of rubber or elastomer. The elastic member 33 may be fixed to the upper plate 4 and the lower plate 5 by baking or by using an adhesive agent, for example.

The transmission member 41 is fixed to a side 4a of the upper plate 4 which opposes a side 4b in which the elastic member 33 is mounted. The transmission member 41 is formed in a tubular shape, from a metal or resin, for example. The transmission member 41 is fixed to the upper plate 4 in a section which includes the central axis 32 of the elastic member 33. The transmission member 41 is a section which receives a load from the receiving member 8 and also can receive a load from both directions of an exterior thereof. For example, if a load is applied to the transmission section 41, received by the receiving member 8, in which the receiving member 8 moves in a direction shown with an arrow 82 shown in FIG. 8, the transmission member 41 will then transmit the load to the elastic member 33 via the upper plate 4. At this point, the upper plate 4 controls unintentional change in shape of the elastic member 3, when the applied load is received by the receiving member 8.

Arrows 83 and 84 shown in the elastic member 33 in FIG. 8, indicate a direction in which the elastic member 33 is compressed or expanded in response to a load applied to the transmission member 41 received by the receiving member 8. In FIG. 8, for example, movement of the elastic member 33 is shown with the respective arrows 83 and 84, when a load is applied in the direction indicated by the arrow 82, received by the receiving member 8 and transmitted to the transmission member 41. As indicated by the arrows 83, a section of the elastic member 33, on a side in front of the direction, being a front side 33A in which a load is applied to the transmission member 41, is compressed. On the other hand, as indicated with the arrows 84, a section of the elastic member 33, on a side which is rear to the direction being a rear side 33B, is expanded. In this way, the elastic member 33 shows opposing movements by either compressing or expanding, depending on whether the section is at the front side 33A or the rear side 33B of the elastic member, when a load is applied from a predesignated direction, to the transmission member 41 received by the receiving member 8.

A compressed volume and expanded volume of the elastic member 33 corresponds to the size of the applied load received by the receiving member 8. The compressed section and expanded section of the elastic member 33 return back to the original form once the applied load, received by the receiving member 8, is released. In this way, the section 33A of the elastic member 33 is compressed by the load applied through the transmission member 41, received by the receiving member 8, and when the second section 33B expands, the compressed section which is 33A generates heat, and the expanded section 33B absorbs heat. As a result heat flows between the lower plate 5 and the base member 2. That is specifically, heat flows from the lower plate 5 towards the base member 2 in a location corresponding to the section that has generated heat, simultaneous to the compression of the elastic member 33. In contrast, heat flows from the base member 2 to the lower plate 5 in a location corresponding to the section which has absorbed heat, simultaneous to the expansion of the elastic member 33.

In the third embodiment, as with the first and second embodiments, the insulating sheet 9, the heat flow sensor 10 and the buffer member 93 provided between the lower plate 5 and the base member 2, are arranged in an order from a side which has the lower plate 5 to a side which has the base section 2, in a vertical axis direction Y thereof. In the third embodiment, the lower plate 5, the insulating sheet 9, the heat flow sensor 10, the buffer member 93 and the base member 2 are adhered to each other by using a double sided tape or an adhesive agent. It is noted that the lower plate 5, the insulating sheet 9, the heat flow sensor 10, the buffer member 93 and the base member 2 may also be fixed by a bolt, for example, that is not shown in the figures. In this case, either of the adhesive agent, double sided tape or bolt are an example of a fixing member.

The heat flow sensor 10, outputs a signal corresponding to heat flowing between the lower plate 5 and the base member 2. As shown in FIG. 9, the heat flow sensors 10 are provided in a plurality of four, for example, disposed around the central axis 32 of the elastic member 33. With further reference to FIG. 9, the heat flow sensors 10 are arranged in four positions around the central axis of the elastic member 33. Specifically, a heat flow sensor 10 provided in a first position diametrically opposed to a second position, with the central axis 32 of the elastic member 33 disposed therebetween, is a first heat flow sensor 11. A heat flow sensor 10 directly opposed to the first heat flow sensor 11 in the second position is a second heat flow sensor 12. Also, a third heat flow sensor 13 and a fourth heat flow sensor 14 are provided in a different positions from the first heat flow sensor 11 and second heat flow sensor 12, in the circumferential direction thereof. The third and fourth heat flow sensors 13 and 14 are also disposed diametrically opposite each other with the central axis 32 of the elastic member 33 disposed between the sensors.

The first to fourth heat flow sensors 11 to 14 respectively, are disposed such that a segment line L1 joining the first and the second heat flow sensors 11 and 12, and a segment L2 joining the third and fourth heat flow sensors 13 and 14 are orthogonal to each other. It is noted that the first to fourth heat flow sensors 11 to 14 respectively, may be disposed in which the segment lines L1 and L2 are intersected at a predetermined angle.

Signals output from the first to fourth sensors 11 to 14 are input into the detector 7.

The detector 7 detects a voltage signal which corresponds to a difference between a thermal electromotive force of the first heat flow sensor 11 and a thermal electromotive force of the second heat flow sensor 12. The voltage signal is referred to as a first signal V1 hereon. The detector 7 also detects a voltage signal which corresponds to a difference between a thermal electromotive force of the third heat flow sensor 13 and a thermal electromotive force of the fourth heat flow sensor 14. This voltage signal is referred to as a second signal V2 hereon.

Specifically, a wiring 23 which has high electric potential when heat flows from the lower plate 5 to the base member 2 via the first heat flow sensor 11, and a wiring 24 which has high electric potential when heat flows from the lower plate 5 to the base member 2 via the second heat flow sensor 12 are connected. Additionally, a wiring 25 which has low electric potential when heat flows from the lower plate 5 to the base member 2 via the first heat flow sensor 11, and a wiring 26 which has low electric potential when heat flows from the lower plate 5 to the base member 2 via the second heat flow sensor 12 are also connected. As a result, a current flows according to a difference between a thermal electromotive force directed to the heat flow sensor 10 which has high electromotive force and thermal electromotive force directed toward the heat flow sensor 10 which has low electromotive force, among the first and second heat flow sensors 11 and 12 respectively, for the wirings 23 and 24. In contrast, a current also flows according to a difference between a thermal electromotive force directed to the heat flow sensor 10 which has low thermal electromotive force and a thermal electromotive force directed to the heat flow sensor which has high thermal electromotive force, among the first and second heat flow sensors 11 and 12 respectively, for the wirings 25 and 26. A detection resistor is therefore connected to the wirings 25 and 26, and by measuring a voltage of both ends of the detector resistor, the detector 7 can detect the first signal voltage V1 as the output corresponding to the difference between the electromotive force of the first heat flow sensor 11 and the second heat flow sensor 12.

The connection of the third heat flow sensor 13 and the fourth heat flow sensor to the wiring 22 is the same as the connection of the first heat flow sensor 11 and the second heat flow sensor 12 described above. As a result, the detector 7 detects the second signal V2 as an output corresponding to a difference between the thermal electromotive forces of the respective third heat flow sensor 13 and the fourth heat flow sensor 14.

Incidentally, heat may flow between the lower plate 5 and the base member 2, for example, due to air flowing around the load change detection apparatus 1, or such other changes of the environment in which the load change apparatus 1 is mounted. The heat flow in this instance, becomes a temperature drift of the output of the first to fourth heat flow sensors 11 to 14 respectively. In this case, the thermal electromotive force of the first to fourth heat flow sensors 11 to 14 show almost the same movement.

In contrast, as described previously, when a load is applied from a predefined direction, with respect to the receiving member 8 and the transmission member 41, the elastic member 33 shows opposing movements by either compressing or expanding in a corresponding section, depending on whether the section is at the front side 33A or the rear side 33B of the elastic member. In this case, the thermal electromotive force of the first heat flow sensor 11 and the thermal electromotive force of the second heat flow sensor 12 thus show opposing movements. The thermal electromotive force of the third heat flow sensor 13 and the fourth heat flow sensor 14 also show opposing movements.

As a result, the detector 7 removes the temperature drift from the output of the first heat flow sensor 11 and the second heat flow sensor 12, based on the first signal V1 corresponding to the difference between the thermal electromotive force of the first heat flow sensor 11 and the second heat flow sensor 12, and can extract an output signal equivalent to component of force of the working load to the elastic member 33, in a parallel direction to the segment line L1 which joins the first heat flow sensor 11 and the second heat flow sensor 12.

The detector 7 also removes the temperature drift from the output of the third heat flow sensor 13 and the fourth heat flow sensor 14, based on the second signal V2 corresponding to the difference between the thermal electromotive force of the third and fourth heat flow sensors 13 and 14, and can extract an output signal equivalent to component of force of the working load to the elastic member 33, in a parallel direction to the segment line L2 which joins the third heat flow sensor 13 and the fourth heat flow sensor 14.

Figure 10:
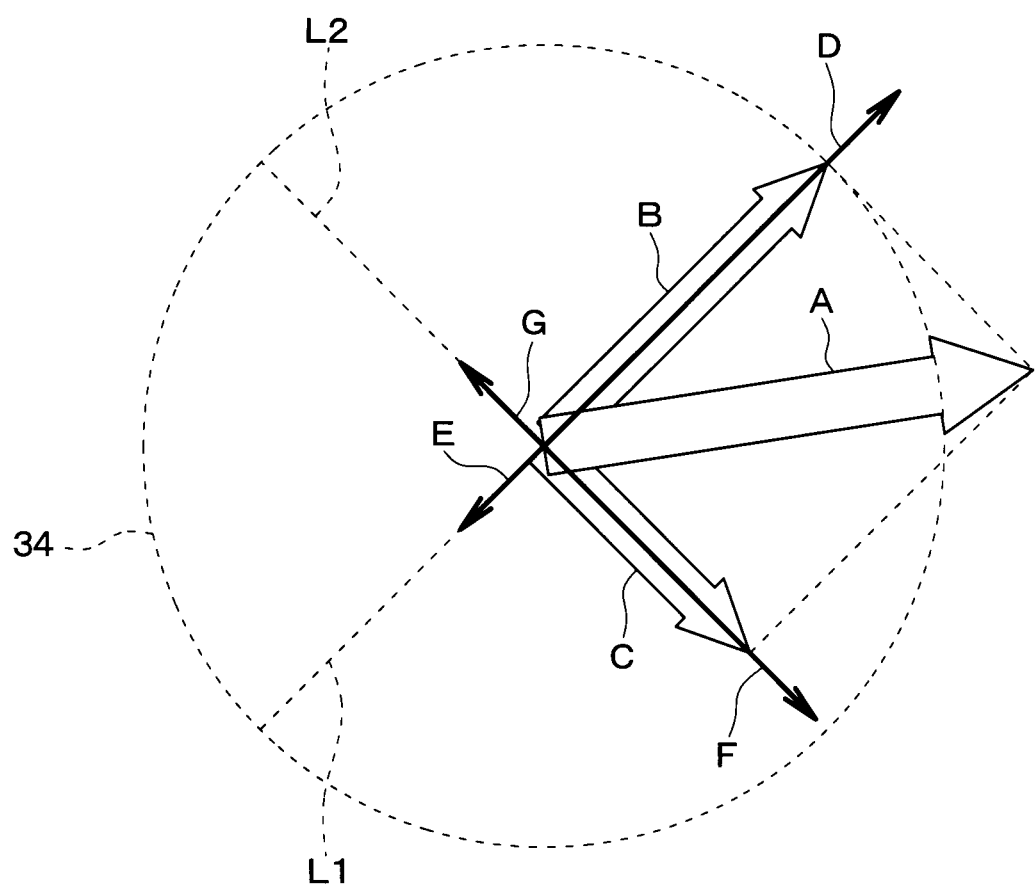
FIG. 10 is a diagram descriptively showing a detection method to detect a direction and a size of a load.

Next, with reference to FIG. 10, a detection method performed by the detector 7, of a working load, is described.

In FIG. 10, a general idea of the elastic member 33 is shown by the broken line 34, when a load is applied. In this case, an example of a load applied in a radial direction of the elastic member 33 is shown by an arrow A. In the example, the load indicated with the arrow A is divided into 2 component forces indicated by arrows B and C. A direction of the arrow B is a direction parallel to the segment line L1 which joins the respective first and second heat flow sensors 11 and 12. In contrast, a direction of the arrow C is a parallel direction to the segment line L2 which joins the respective third and fourth heat flow sensors 13 and 14.

A general idea of relative thermal electromotive force of the first heat flow sensor 11 and the second heat flow sensor 12 is also shown by respective arrows D and E, in the same example shown in FIG. 10. As described above, the first signal V1 is the output corresponding to the difference between the thermal electromotive force of the first heat flow sensor 11 and the second heat flow sensor 12. The first signal V1 is equivalent to the component force B of the load applied in the radial direction of the elastic member 33, in the parallel direction to the segment line L1 which joins the first heat flow sensor 11 and the second heat flow sensor 12.

A general idea of relative thermal electromotive force of the third heat flow sensor 13 and the heat flow sensor 14 is also shown by respective arrows F and G, in the same example shown in FIG. 10. As described above, the second signal voltage V2 is the output corresponding to the difference between the thermal electromotive force of the third heat flow sensor 13 and the fourth heat flow sensor 14. The second signal V2 is equivalent to a component of force C of the load applied in the radial direction of the elastic member 33, in the direction parallel to the segment line L2, which joins the third and fourth heat flow sensors 13 and 14. As a result, the detector 7 detects the direction of a load A, that is a direction in which the load is applied, and the size of the load which works the elastic member 33, by addition of two component of forces B and C.

Effect of the load change detection apparatus 1 according to the third embodiment will now be described.

(Effect 1)

The elastic member 33 according to the third embodiment is rubber or elastomer fixed to a surface of the lower plate 5 on the side thereof which opposes the base member 2.

As a result, rubber or elastomer undergoes elastic deformation of the elastic member 33, according to a load change applied received by the receiving member 8, and either generates or absorbs heat. The load change detection apparatus 1 detects the size or the direction of the load change applied to the receiving member 8 by using a physical characteristic of the elastic member 33.

(Effect 2)

In the third embodiment, the load change detection apparatus 1 is also provided with the transmission member 41 which transmits the applied load, received by the receiving member 8, to the elastic member 33.

As a result, since the elastic member does not directly receive the applied load change, received by the receiving member 8, damage thereof can be prevented. Additionally, unintentional deformation of the elastic member 33 from the load applied received by the receiving member can be controlled by the transmission member 41 and the upper plate 4.

(Effect 3)

The transmission member 41 is fixed to the elastic member 33 at the section which includes the central axis 32.

As a result, when a load is applied from the receiving member 8, in the predetermined direction of the transmission member 41, the elastic member 33 shows opposing movement by compressing or expanding at the respective front side 33A and the rear side 33B in the predetermined direction. Furthermore, by mounting the plurality of heat flow sensors 10 in the circumferential position of the central axis 32 of the elastic member 33, output of each of the heat flow sensors 10 is different from another heat flow sensors 10, among the first to fourth heat flow sensors, 11 to 14 respectively. The load change detection apparatus 1 can therefore detect the direction and the size of the load change, received by the receiving member 8, applied to the transmission member 41, by performing, for example, calculation based on the output of the plurality of heat flow sensors 10.

(Effect 4)

In the third embodiment, the plurality of heat flow sensors 10 are provided around the central axis 32 of the elastic member 33.

Each of the plurality of heat flow sensors 10, output different signals according to the direction of the load change, received by the receiving member 8 and applied to the elastic member 33. The load change detection apparatus 1 can thus detect the direction and the size of the load change applied to the elastic member 33 received by the receiving member 8, based on the output of the plurality of heat flow sensors 10.

(Effect 5)

In the third embodiment, the first heat flow sensor 11 and the second heat flow sensor 12 are positioned diametrically opposite each other, with the central axis 32 of the elastic member 33 disposed therebetween. The detector 7 detects the direction and the size of the load change applied to elastic member 33 based on the output corresponding to the difference between the thermal electromotive force of the first heat flow sensor 11 and the second heat flow sensor 12.

According to the described configuration, when a load change is applied in one direction of the first heat flow sensor 11 and the second heat flow sensor 12, the thermal electromotive force of the heat flow sensor 10 which is disposed at the front side of the load increases. In contrast, thermal electromotive force of the heat flow sensor 10 disposed at the rear side of the load decreases. As a result, the detector 7 can detect the size and the direction of the working load change applied to the elastic member 33.

Additionally, due to change of temperature in the environment, for example, if temperatures of components configuring the load change detection apparatus 1 change at the same time, the thermal electromotive forces of the two heat flow sensors will also change temperature at the same time. That is, movement of the thermal electromotive force of the two heat flow sensors 10 are different when the working load is applied to the elastic member 33, and the movement of the thermal electromotive force of the two heat flow sensors is the same when there is a change of temperature in the environment, for example. Due to the reasons described above, the detector 7 decreases the temperature drift caused by the temperature change of the environment, for example, and can detect the working load change applied to the elastic member 33, based on the output corresponding to the thermal electromotive force difference between the two heat flow sensors.

(Effect 6)

In the third embodiment, the plurality of heat flow sensors 10 are arranged so that the third heat flow sensor 13, provided to intersect the line segment L1 joining the first and second heat flow sensor 11 and 12, and the fourth heat flow sensor 14 are positioned diametrically opposite each other, with the central axis 32 of the elastic member 33 disposed therebetween. The detector 7 detects the direction and the size of the load change applied to the elastic member 33, based on the first signal V1 for the output corresponding to the thermal electromotive difference between the first and the second heat flow sensors 11 and 12, and the second signal V2 for the output corresponding to the thermal electromotive difference between the third and the fourth heat flow sensors 13 and 14.

As a result, when a predetermined load, received by the receiving member 8, is applied in the predetermined direction of the elastic member 33, the first signal V1 is equivalent to a component of force in the parallel direction of the line segment L1 joining the first heat flow sensor 11 and the second heat flow sensor 12, of the load applied thereof to the elastic member 33. In contrast, the second signal V2 is equivalent to a component of force in the parallel direction of the segment line L2, joining the third heat flow sensor 13 and the fourth heat flow sensor 14, of the load applied thereof. The detector 7 can thus detect the direction and the size of the load changed applied to the elastic member 33, by the addition of the two component of forces detected, based on the respective first signal V1 and second signal V2.

Fourth Embodiment

The fourth embodiment of the present disclosure will now be described. The load change detection apparatus 1 according to the fourth embodiment may be used by a joystick, for example, provided for a user to provide input into a computer. The user moves a cursor on a screen of the computer using the joy stick. In the fourth embodiment, operation performed by the user may be an example of the receiving member 8.

Figure 11:
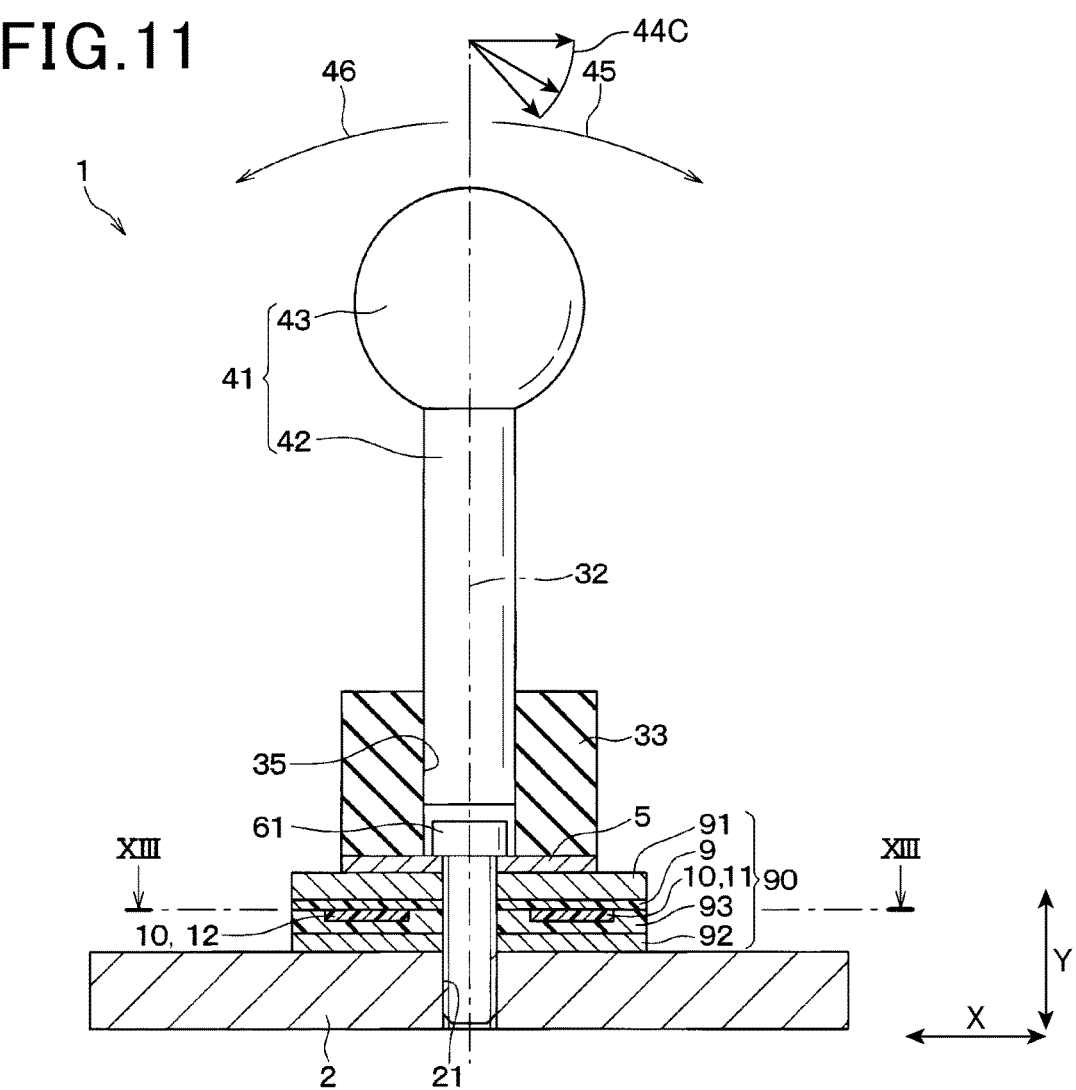
FIG. 11 is a cross sectional configuration showing a load change detection apparatus according to a fourth embodiment.

As shown in FIG. 11, in the fourth embodiment, the elastic member 33 is a tubular shape, formed from rubber containing an ester type of polyurethane, for example. More specifically, the elastic member has a hollow rubber formation. The elastic member 33 is fixed to the plate member 5 by baking or by using an adhesive agent.

The transmission member 41 is configured of a stick section 42 and a grip ball 43. The stick section 42 is inserted through a hole section 35 provided in the section which includes the central axis 32 of the elastic member 33, and fixed therein by close fitting into the hole member 35. The transmission member 41 can move the grip ball 43 in a circumferential direction 44C or radial direction of the tubular elastic member 33, with a central area of the lower plate 5 as a center point, that is, the user can freely operate the transmission section 41.

The lower plate 5 provided with the elastic member 33 mounted thereon, is fixed to a base plate as the base plate 2, using a fastening bolt 61, via a washer-shaped sensor unit 90. The fastening bolt 61 is inserted through the hole provided on the lower plate member 5 and the second hole provided on the washer shaped sensor unit, and then screwed into the screw hole 21.

Figure 12:
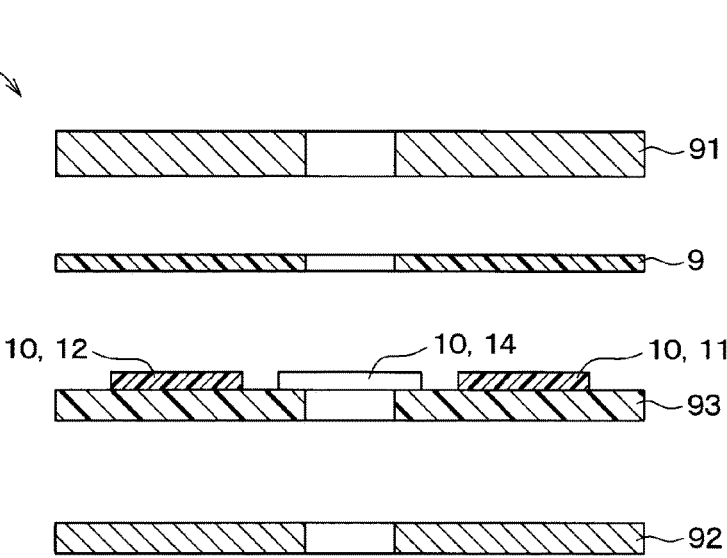
FIG. 12 is an exploded cross sectional view showing washer shaped sensor unit of the load change detection apparatus according to the fourth embodiment.

An exploded cross sectional view showing a washer shaped sensor is shown in FIG. 12.

The washer shaped sensor unit 90 is configured of a first metal washer 91, the insulating sheet 9, the plurality of heat flow sensors 10, the buffer member 93 and a second metal washer 92, for example. The first metal washer 91, the insulating sheet 9, the buffer member 93 and the second metal washer 92 are formed in a circular shape.

Figure 13:
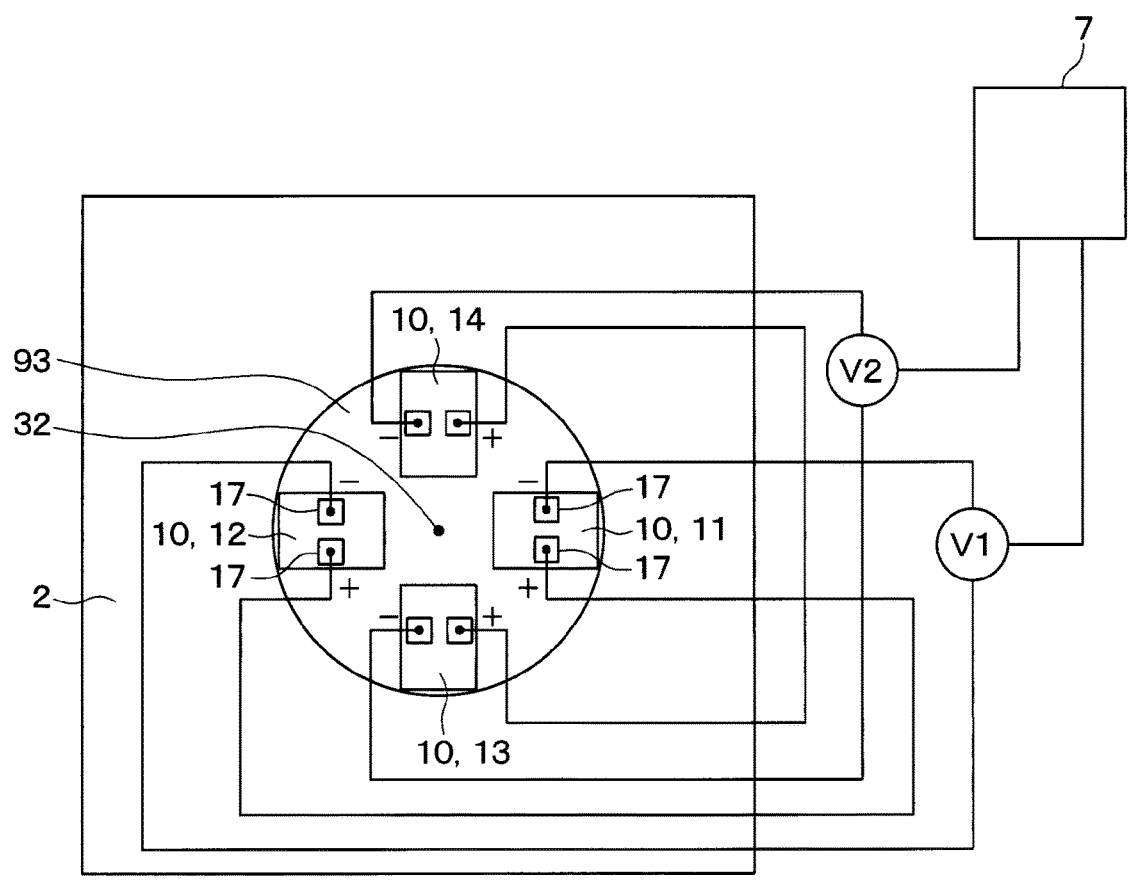
FIG. 13 is cross sectional view across a line XIII-XIII shown in FIG. 11.

The plurality of heat flow sensors 10 are attached to the buffer member 93. As shown in FIG. 13, the plurality of heat flow sensors 10 are connected by the same wire connection method described in the third embodiment. The plurality of heat flow sensors 10 are provided with each of the respective terminals 17 connected to the wiring 22, with the insulating sheet 9 covering a surface thereof, as shown in FIG. 12.

The insulating sheet 9 is the same resin sheet described in embodiments 1 to 3, formed of polyimide, for example. The resin sheet 9 blocks electric conduction between the heat flow sensors 10 and the terminals 17 thereof, and the first metal washer 91, as shown in FIG. 12.

The buffer member 93 is formed from fluorocarbon resin sheet, for example, polytetrafluoroethylene. The buffer member 93 absorbs unevenness due to the terminal 17, provided on the surface of the heat flow sensor 10, or the wiring 22 connected to the terminal 17, and also by the solder which connects the terminal 17 and the wiring 22. It is noted that the buffer 93 is compressed to a predetermined thickness by a pressing process, in order to obtain an optimum soft texture for use.

The plurality of heat flow sensors 10 are sandwiched between the insulating sheet 9 and the buffer member 93, and further between the first metal washer 91 and the second metal washer 91, in the respective up-down direction. The first and second metal washers 91 and 92 function as protection plates to prevent damage to the plurality of heat flow sensors 10, and also as transmission members to allow heat to flow through in a thickness direction thereof.

The first metal washer 91, the insulating sheet 9, the plurality of heat flow sensors 10, the buffer member 9 and the second metal washer 92 are joined to each other by double sided tape (omitted from the figures).

The washer shaped sensor unit 90 having a typical washer shape, is a standard sensor unit in which various equipment and machines can easily be incorporated therein. That is, various load change detection apparatuses can be mounted thereon.

As shown in FIG. 13, signals output from the four heat flow sensors, which configure the washer shaped sensor unit 90, are input into the detector 7.

Figure 14:
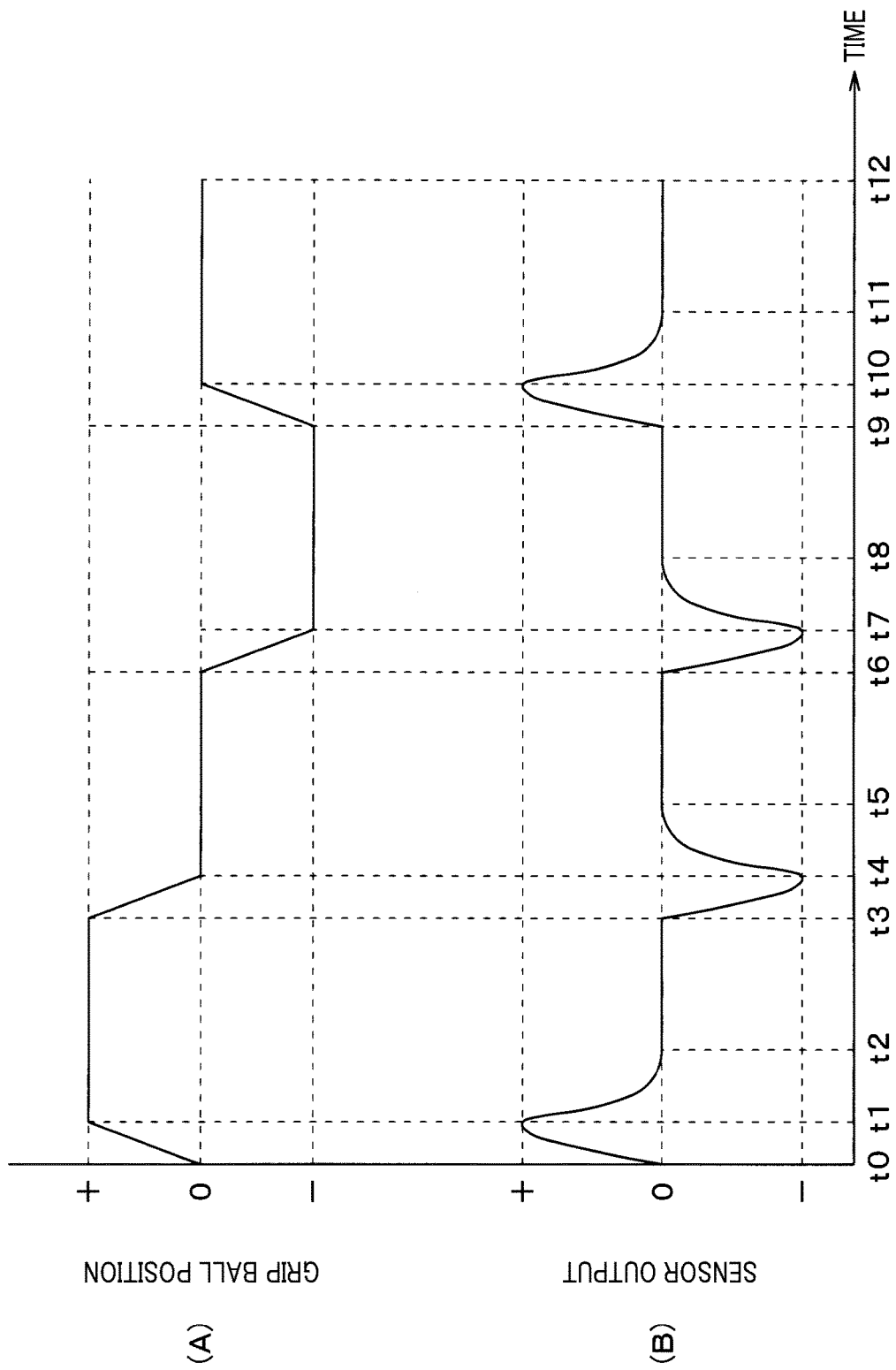
FIG. 14 shows a relation of a position of a grip ball and a sensor output of the load change detection apparatus.

FIG. 14 (A) shows a relationship between a position of a grip ball and a sensor output of the load change detection apparatus. The signal of the grip ball 43 when the user moves the grip ball 43 of the transmission member 41, to incline in the direction shown by the arrow 45 or shown by the arrow 46 shown in FIG. 11. It is noted that the respective arrows 45 and 46 represent opposing directions thereof.

Additionally in FIG. 14 (A), '0' represents a position of the grip ball 43, when the user corrects the grip ball 43 from the inclined position to an upright position thereof, with respect to the elastic member 33. A '+' sign represents the position of the grip ball 43 when grip ball 43 is moved to a predetermined angle in the direction shown by arrow 45 in FIG. 11. In contrast, a '−' sign represents the position when grip ball 43 is moved to a predetermined angle in the direction shown by arrow 46 in FIG. 11.

FIG. 14 (B) shows output of the first signal V1 as the output corresponding to the difference between the thermal electromotive forces of the first heat flow sensor 11 and the second heat flow sensor 12, among the four heat flow sensors 10.

Now referring back to FIG. 11, the first heat flow sensor 11 is disposed at a front-end side of the arrow 45 and the second heat flow sensor 12 is disposed at a front-end side of the arrow 46, with respect to the central axis 32.

Hereinafter, a section located at the front-end side direction of the arrow 45 is referred to as 'a first section of the elastic member 33'. A section located at a rear end side direction of the arrow 45 is referred to as 'a second section of the elastic member 33'.

In FIG. 14 (B) a vertical axis represents the sensor output and a horizontal axis represents time. With reference to FIG. 14 (A), from time 't0' to 't1' when the user inclines the grip ball 43 in the direction indicated with the arrow 45 in FIG. 11, the output of the first signal V1 increases to a '+' side thereof. That is, in inclining the grip ball 43 in the direction of the arrow 45, the first section of the elastic member 33 is compressed and generates heat, whereas the second section of the elastic member 33 expands and absorbs heat. As a result, heat flows from the first section of the elastic member 33, and passes through the first heat flow sensor 11 to the base member 2. On the other hand, heat flows from the base member 2, passes through the second heat flow sensor 12 to the second section of the elastic member 33. At this point, the thermal electromotive force of the first and second heat flow sensors 11 and 12 are opposed to each other. The first signal V1 is the output corresponding to the difference between the thermal electromotive forces of the first heat flow sensor 11 and the second heat flow sensor 12, the output itself is increased to the '+' side thereof.

As shown in FIG. 14 (A), from the time t1 to the time t3, the position of the grip ball 43 is fixed. At this point, as shown in FIG. 14 (B), from the time t1 to t2 the output of the first signal V1 returns to 0. That is, if the grip ball 43 is in a fixed position, the heat of the first section of the elastic member 33 is also dissipated to the base member 2 and air, for example, and heat flowing to the base member 2 through the first heat flow sensor 11 decreases. Additionally, an influx of heat also flows from the base member 2 and air, for example, to the second section of the elastic member 32. This heat passes through the second heat flow sensor 12 from the base member 2, and heat flowing to the second section of the elastic member 33 decreases. The output of the first signal V1 thus decreases.

From the time t3 to t4, once the user returns the position of the grip ball 43 from the inclined position in the direction of the arrow 45, shown in FIG. 11, to the upright position thereof, as shown in FIG. 14(B), the output of the first signal V1 increases to the '−' side over the time t3 to t4. That is, when the grip ball 43 is returned to the upright position from the inclined position in the direction of the arrow 45 shown in FIG. 11, the first section of the elastic member 33 absorbs heat since the first section returns to an original state from a compressed state. The original state refers to a state of the first section of the elastic member 33 before a load change is applied to the transmission member 41 received by the receiving member 8. Additionally, a compressed state refers to compression of the first section of the elastic member 33 when a load is applied. As a result, heat flows from the base member 2, and passes through the first heat flow sensor 11 to the first section of the elastic member 33. In contrast, the second section of the elastic member 33 changes from an expanded state to the compressed state thus generating heat. As a result, heat flows from the second section of the elastic member 33, and passes through the second heat flow sensor 12 to the base member 2. The output of the first signal V1 thus increases to the side thereof. The expanded state refers to expansion thereof.

From time t4 to t6, the grip ball 43 is in a fixed position due to the user. As shown in FIG. 14 (B), from t4 to t5 the first signal V1 returns to 0. If the grip all 43 is in a fixed state, heat flowing from the base member 2, passing through the first heat flow sensor 11 to the first section of the elastic member 33 decreases, and heat flowing from the second section of the elastic member 33, passing through the second heat flow sensor 12 to the base member 2 also decreases. Thus, the output of the first signal V1 will also decrease as a result.

From the time t6 to t7, the user inclines the grip ball 43 in the direction of the arrow 46, shown in FIG. 11, and the first signal V1 increases to the '−' side thereof, as shown in FIG. 14(B). In this case, when the user inclines the grip ball 43 in the direction of the arrow 46, the second section of the elastic member 33 is compressed and generates heat, and the first section of the elastic member is expanded and absorbs heat. As a consequence, heat flows from the second section of the elastic member 33, and passes through the second heat flow sensor 12 to the base member 2, and in contrast, heat flows from the base member 2, and passes through the first heat flow sensor 11 to the first section of the elastic member 33, as a result. The output of the first signal V1 is thus increased to the '−' thereof.

From time t7 to t9, the user has the grip ball 43 in a fixed position as shown in FIG. 14(A). At this point, with reference to FIG. 14 (B), from the time t7 to t8, the first signal V1 returns to 0. At this point, since the grip all 43 in a fixed state, heat flowing from first section of the elastic member 33, passing through the second heat flow sensor 12 to the base member 2 decreases, thus the output of the first signal V1 will also decrease as a result.

With reference to FIG. 14(A), from the time t9 to t10, the user returns the grip ball 43 to the upright position from the inclined position in the direction indicated with the arrow 46 shown in FIG. 11, and the output or the first signal V1 increases to the '+' side thereof, as shown in FIG. 14(B). That is, once the user returns the grip ball 43 to the upright position from the inclined position in the direction indicated with the arrow 46, the second section for the elastic member 33 returns to the original state from the compressed state thus absorbing heat. As a consequence heat flows from the base member 2, and passes through the second heat flow sensor 12 to the second section of the elastic member 33. In contrast, the first section of the elastic member 33 changes from the expanded state to the compressed state thus generating heat. As a result, heat flows from the first section of the elastic member 33, passes through the first heat flow sensor 11 to the base member 2 and the output of the first signal V1 increases to the '+' side thereof.

With reference to FIG. 14 (A), from the time t10 to t12, the user has the grip ball 43 is in the fixed position. As shown in FIG. 14(B), from t10 to 11 the first signal V1 returns to 0. If the grip ball 43 is in the fixed state, heat flowing from the base member 2, passing through the second heat flow sensor 12 to the second section of the elastic member 33 decreases, and as the heat flowing from the first section of the elastic member 33, passing through the first heat flow sensor 11 to the base member 2 also decreases, the output of the first signal V1 is decreased as a result.

The output of the first signal V1 when the user inclines the grip ball 43 of the transmission member 41 in the directions indicated by the arrows 45 and 45 shown in FIG. 11 has been described based on FIGS. 14(A) and (B). Incidentally, in the fourth embodiment also, the detector 7 detects the second signal V2 as the output corresponding to the difference between the thermal electromotive force of the respective third and fourth heat flow sensors 13 and 14, in addition to the detection of the first signal. The detector 7 can detect the direction and the size of the load change applied to the elastic member 3 based on the first and second signals V1 and V2, according to the same method described in the third embodiment. The user can thus move the cursor on the screen of the computer by using the joy stick.

The load change detection apparatus 1 according to the fourth embodiment elicits the following effects in addition the effects described in embodiments 1 to 3.

(Effect 1)

In the fourth embodiment, the stick member 42 of the transmission member 41 is passed through the hole member 35 provided on the section which includes the central axis 32 of the cylindrical elastic member 33, and is fixed therein by closely fitting into the hole member 35.

In the configuration described, the transmission member 41 can be firmly fixed onto the elastic member 33. Additionally, a load change applied from the user, which is the receiving member 8, to the transmission member 41, can reach a center section of the elastic member 33 with high certainty, and an entirety of the elastic member 33 can be expanded or compressed.

(Effect 2)

In the fourth embodiment, the plurality of heat flow sensors 10 are disposed between the insulator sheet 9 and the buffer member 93. Furthermore, the first metal washer 91 and the second metal washer 92 are disposed in the respective upper and lower positions of the insulator sheet 9 and the buffer member 93. In the configuration, the first and second metal washers 91 and 92 function as protectives plates to prevent the heat flow sensors 10 from being damaged, and also function as conduction members which allow the heat flow to pass therethrough in a thickness direction thereof.

As a result, the stress occurring when the elastic member 33 elastically deforms is not directly transmitted to the heat flow sensors 10. Furthermore, even if an additional impact is applied to the elastic member 33 received by the receiving member 8, damage to the heat flow sensors 10 from the impact is avoidable.

In providing the heat flow sensors 10 as the washer shape sensor unit 90, a standard sensor unit in which various equipment and devices can be easily incorporated therein can be configured.

Fifth Embodiment

The fifth embodiment of the present disclosure will now be described. Incidentally, the fifth embodiment is a modified example of the third embodiment.

Figure 15:
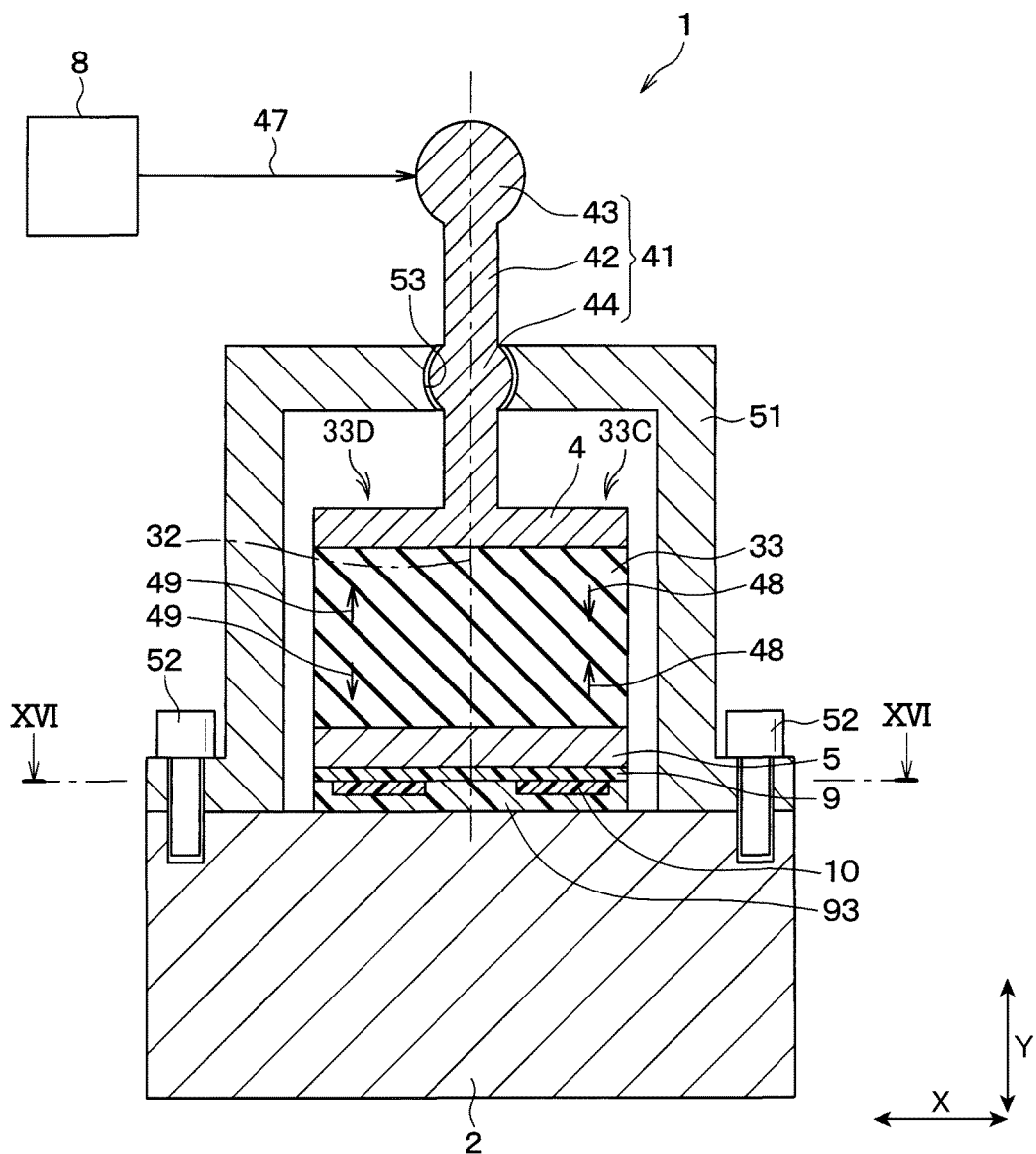
FIG. 15 is a cross sectional view showing a load change detection apparatus according to a fifth embodiment.

As shown in FIG. 15, in the fifth embodiment, the load change detection apparatus 1 is equipped with a cover member 51 on an external side of the elastic member 33. The cover member 51 is fixed to the base member 2 by a bolt 52. In contrast the transmission member 41 is fixed to the upper plate 4, and additionally provided with an oval section 44 disposed in a center section of the stick member 42. The stick member 42 is disposed to extend in an axial direction from the upper plate 4. The cover member 51 is provided with a lock section 63 to lock the oval section 44. The transmission member 41 is configured so that the oval section 44 is locked by the lock member 53 of the cover member 51, and can be oscillated with the oval section 44 as a center part.

The cover member 51 locks the oval member 44 of the transmission member 41 using the locking member 53 and is fixed to the base member 2 by the bolt 52, with the elastic member 33 compressed to the side of the base member 2 via the upper plate 4 in which the transmission member 41 is fixed to thereon. The elastic member 33 is mounted on the base member 2, is compressed between the upper plate 4 and the base member 2.

In FIG. 15, physical movements of the elastic member are shown by arrows 48 and 49, when a load received by the receiving member 8 is applied in a direction indicated by arrow 47, for example, to the transmission member 41. Specifically, as indicated by the arrow 48, a section of the elastic member 33 is compressed, the section being at the front side 33C in which a load is applied to the transmission member 41. In contrast, as indicated by the arrows 49, a section of the elastic member 33, expands in order to return to an original state from the compressed state. The rear side which expands is the rear side 33D. In this way, the elastic member 33 shows opposing movements by either compressing or expanding, depending on whether the section is at the front side 33C or the rear side 33D of the elastic member, when a load, received by the receiving member 8, is applied from a predesignated direction (arrow 47) to the transmission member 41.

Figure 16:
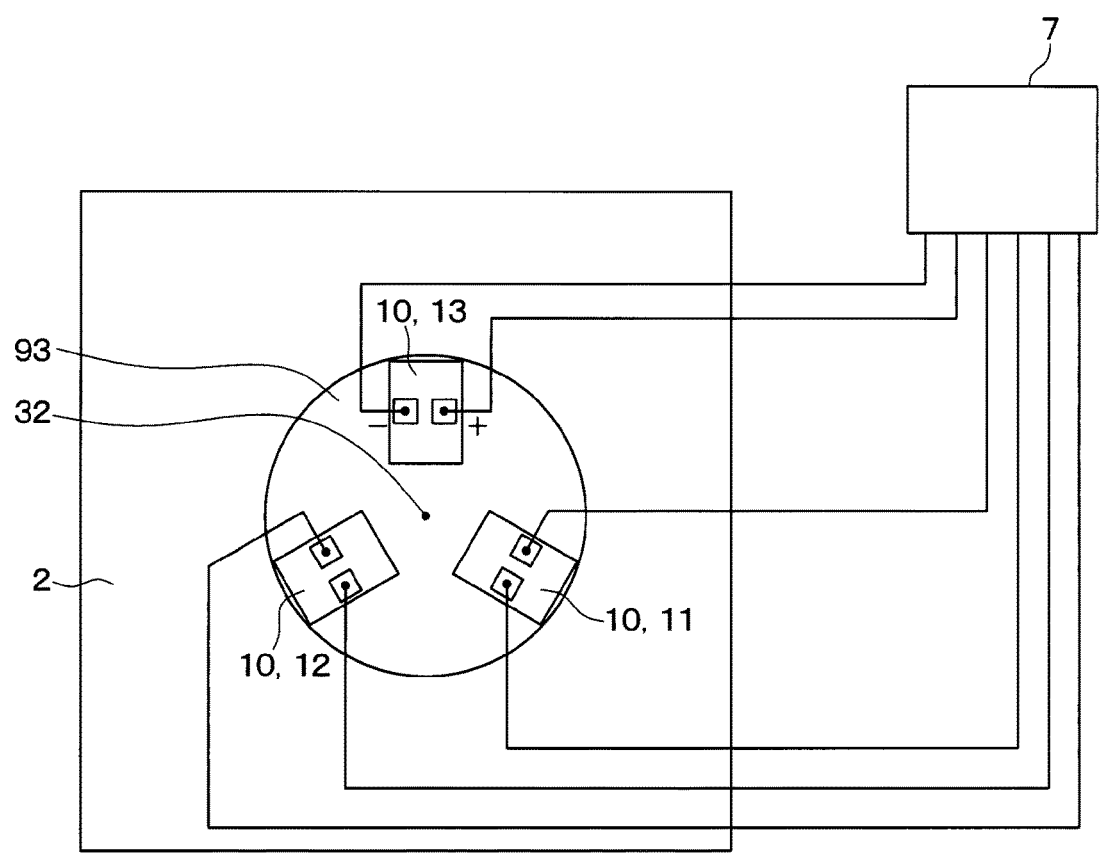
FIG. 16 is a cross sectional view across a line XVI-XVI shown in FIG. 15.

As shown in FIG. 16 in the fifth embodiment, for example, three heat flow sensors 10 are provided in a circumferential direction of the central axis 32 of the elastic member 32. It is noted that that, the cover member 51 is omitted from FIG. 16 for convenience. Hereinafter, the three heat flow sensors 10 are referred to as the first, second and third heat flow sensors 11, 12 and 13 respectively.

Each signal output by the first to the third heat flow sensors 11 to 13, are input into the detector 7. The detector 7 calculates a difference between the signals output therefrom the heat flow sensors 11 to 13. The detector 7 can remove the temperature drift from the output signals, and extract output signals equivalent to a load change applied to the grip ball 43 of the transmission member 41. The detector 7 can thus detect the size and the direction of a load change applied to the elastic member 33, based on the output from the heat flow sensors 11 to 13, in the fifth embodiment also.

The load change detection apparatus 1 in the fifth embodiment elicits the same effects as the load change detection apparatus 1 described in embodiment 1 to 4.

Other Embodiments

It should be understood that the foregoing relates only the preferred embodiments of the invention, and that it is intended to cover all modifications accordingly without departing from the scope of the claims. The configuring elements described in the preferred embodiments are not necessarily essential elements unless stated otherwise. Furthermore, a number, quantity, value and range, for example of the configuring elements are not limited to those described in the preferred embodiments, unless specifically stated otherwise. A form or a position of the configuring elements in the preferred embodiment is not limited to the described unless stated otherwise.

In each of the embodiments described above, the load change detection apparatus 1, provided with the heat flow sensors 10 configured as shown in FIG. 4 and FIG. 5, is used, however not limit to the described. That is, other configurations may also be incorporated.

In the embodiments, the load change detection apparatus 1 provided with 1 to 4 heat flow sensors 10 is described, however the heat flow sensor 10 may be provided in a plurality of 5 or more.

In other embodiments, the load change detection apparatus 1 may be provided with the base member 2 or the lower plate 5 having a concave section, and the heat flow sensors 10 may be embedded in the concave section.

In the fourth embodiment, the elastic member 33 is formed from rubber containing an ester type polyurethane, however in the other embodiments the elastic member 33 may be formed from various synthesized rubber materials or natural rubber materials, in addition to rubber containing an ester type polyurethane.

In the other embodiments, the base member 2, the upper plate 4, the lower plate 5 and the screw member 6 are not limited to metal, and may be formed from resin, for example.

In summary, according to a first aspect shown in a part of or all of the embodiments, the load change detection apparatus is provided with a base member, an elastic member, a lower plate, a fixing member and a heat flow sensor. The elastic member elastically deforms according to an applied load change received by the receiving member. The lower plate and the elastic member are fixed to the base member. The heat flow sensors provided between the base member and the lower plate, output signals corresponding to heat flowing between the lower plate and the base member, due to generated heat or absorbed heat when the elastic member elastically deforms.

As a result, when the elastic member changes the elastic shape thereof according to the load change applied, heat flows between the lower plate and the base member corresponding to the heat generated or absorbed at the elastic member. In turn, the heat flow sensors provided between the lower plate and the base member output signals corresponding to the heat flow. The signals correspond to a size of formational change of the elastic member, which in turns corresponds to load change applied to the elastic member, received by the receiving member. As a result, the load change apparatus can thus detect a size of the load change which is applied by the receiving member.

The stress occurring when the elastic member changes the elastic shape thereof is shut off by the lower plate and is not directly transmitted therefrom to the heat flow sensors. As a result, even if an additional impact is applied to the elastic member received by the receiving member, damage to the heat flow sensors is avoided. Thus, malfunction of the heat flow sensors from the load change applied to the receiving member is also prevented.

According to a second aspect of the present disclosure, the elastic member is rubber or elastomer fixed to the surface of the lower plate (first plate), which opposes the side of the base member.

The rubber or the elastomer changes elastic shape thereof, according to a load change applied received by the receiving member, and thus generates or absorbs heat. The load change detection apparatus detects a size and direction of the applied load change, received by the receiving member, by using physical characteristics of the elastic member.

In a third aspect, the load change detection apparatus is also provided with the transmission member which transmits a load change applied to the elastic member received by the receiving member.

According to the configuration, since the load change applied to the receiving member is not directly transmitted to the elastic member, damage thereof can be prevented. Additionally, unintentional deformation of the elastic member due to the applied load received by the receiving member can be controlled by the transmission member.

In a fourth aspect of the present disclosure, the transmission member is fixed to the central axis of the elastic member.

As a result, when a load is received by the receiving member and to the transmission member in a predetermined direction, the sections which are respectively the front side and the rear side of the elastic member, show opposed movements by either compression or expansion. As a result, if the plurality of heat flow sensors are disposed circumferentially around the central axis the elastic member, the output from each of the heat flow sensors 10 is different from other heat flow sensors, among the plurality of heat flow sensors provided. The load change detection apparatus can thus detect the size and the direction of the load change, received by the receiving member, and applied to the transmission member, by performing calculation based on the output from the plurality of heat flow sensors.

According to a fifth aspect of the present disclosure, the transmission member is inserted through the hole section provided on a section which includes the central axis of the elastic member.

As a result, the transmission member is firmly fixed to the elastic member and a load change received by the receiving member, and applied to the transmission member, can reach the center section of the elastic member with high certainty, and an entirety of the elastic member 33 can be expanded or compressed.

In a sixth aspect of the present disclosure, the load change detection apparatus is provided with the upper plate which supports the side of the elastic member which opposes the side of the base member.

According to the configuration, when a load is applied to the elastic member, received by the receiving member, deformation, that is, change of the elastic shape of the elastic member is controlled, and unintentional change of the shape can be prevented.

In the seventh aspect of the present disclosure, the load change detection apparatus is provided with a cover member which locks a section of the transmission. The cover member is fixed to the base member, with the elastic member compressed to the side of the base member, through the upper plate which is fixed to the transmission member.

As a result, the load change detection apparatus can be provided with the elastic member in a compressed state mounted on the base member through the cover.

In an eighth aspect of the present disclosure, the load change detection apparatus is equipped with the buffer member provided at least between the heat flow sensor and the lower plate, or between the heat flow sensor and the base member.

As a result even if the surface of the heat flow sensor, for example, is uneven, the buffer member absorbs the unevenness, thus the lower plate, the heat flow sensor, and the buffer member are closely adhered to each other. As a result, the load change detection apparatus can thus increase the output of the heat flow sensors by improving the heat flow between each of the components.

According to a ninth aspect of the disclosure, the plurality of heat flow sensors are provided circumferentially around the central axis the elastic member.

As a result, if the elastic member is rubber or elastomer, a section that compresses and a section that expands circumferential to the center axis thereof, are each formed on the elastic member, according to a load, received by the receiving member and applied to the elastic member, in the predetermined direction thereof. Furthermore, in providing the plurality of heat flow sensors disposed in the circumferential direction of the center axis, each heat flow sensor 10 output different signals corresponding to a load change applied to the elastic member. The load change detection apparatus can therefore detect the size and the direction of the load applied to the elastic member from the receiving member, based on the output from the plurality of the heat flow sensors.

In a tenth aspect of the present disclosure the load change detection apparatus is further provided with the detector which detects the size and direction of the load change applied to the elastic member, based on the output of the plurality of heat flow sensors.

As a result, the load change detection sensor may be provided with a detector which performs calculations based on the output of the plurality of heat flow sensors.

An eleventh aspect of the present disclosure is the plurality of heat flow sensors are the first heat flow sensor and the second heat flow sensor. The first heat flow sensor and the second heat flow sensor are provided diametrically opposite to each other, with the central axis of the elastic member provided therebetween. The detector detects the size and the direction of the load change applied to the elastic member, based on the output corresponding to the difference between the thermal electromotive force of the first heat flow sensor and the second heat flow sensor.

According to the configuration, when the load change is applied to the elastic member, a direction in which the heat flow passes through the first heat flow sensor is opposite to the direction in which the heat flow passes through the second heat flow sensor, due to compression of the front side thereof, and also due to the rear side returning to the original form from either the expanded or the compressed state. As a result, the detector can detect the size and the direction of the load change applied to the elastic member, based on the output corresponding to the difference between the thermal electromotive force of the first heat flow sensor and the second heat flow sensor 12.

Additionally, due to change of temperature in the environment, for example, if the temperature of the base member or the elastic member changes at the same time, the heat flow passing through the first and the second heat flow sensors, flows in a same direction and with a same amount. As a result, the thermal-electromotive forces of the first and second heat flow sensors will also change in the same manner. The detector can thus decrease the temperature drift occurring due to a change of the temperature in the environment, based on the output corresponding to the difference between the thermal electromotive force of the two heat flow sensors.

According to another aspect of the present disclosure, the plurality of heat flow sensors are arranged so that third heat flow sensor, provided to intersect with the line segment joining the first and second heat flow sensors, and the fourth heat flow sensor are positioned diametrically opposite each other, with the central axis of the elastic member 33 therebetween the sensors. The detector detects the direction and the size of the load change applied to the elastic member, based on the first signal for the output corresponding to the thermal electromotive force difference between the first and second heat flow sensor, and the second signal for the output corresponding to the thermal electromotive difference between the third and fourth heat flow sensors.

According to the configuration, when a predetermined load received by the receiving member is applied in the predetermined direction of the elastic member, the first signal is equivalent to a component of force in the parallel direction of the line segment joining the first heat flow sensor and the second heat flow sensor, of the load applied to the elastic member. In contrast, the second signal is equivalent to a component of force in the parallel direction of the segment line joining the third heat flow sensor and the fourth heat flow sensor, of the load applied thereof. The detector can thus detect the direction and the size of the load change applied to the elastic member 33 by the addition of the detected two component of forces based on the respective first signal and second signal.

In a thirteenth aspect of the present disclosure, the heat flow sensors are disposed circumferentially around the center axis of the fixing member.

In the configuration, the output of the sensors can be increased by increasing the area of the heat flow sensors.

In a fourteenth aspect, the elastic member is the cantilever beam member extended from the lower plate to the exterior side thereof.

DESCRIPTION OF SYMBOLS

The cantilever beam member undergoes elastic deformation according to the load change applied received by the receiving member, and generates or absorbs heat. The heat flow sensor outputs the signal corresponding the heat flowing between the lower plate and the base member, when the cantilever generates or absorbs heat. The load change detection apparatus can thus detect the size of the load change applied to the receiving member.

REFERENCE SYMBOLS

1 Load change detection apparatus, 2 base member, 3, 33 elastic member, 5 lower plate, 6 fixing member, 8 receiving member, 10 to 14 heat flow sensors.

What is claimed is:

1. An apparatus for detecting changes in load applied thereto, comprising:
   a base member;
   an elastic member elastically deforming;
   a first plate supporting a surface of the elastic member;
   a fixing member fixing the first plate and the elastic member to the base member, and
   heat flow sensors;
   wherein
   the elastic member elastically deforms according to a change of a load that is a load change, applied to a receiving member which receives the load;
   the first plate supports the surface of the elastic member which is the surface disposed on a side of the base member; and
   the heat flow sensors, disposed between the base member and the first plate, output signals corresponding to heat flowing between the first plate and the base member, due to heat generation or heat absorption when the elastic member elastically deforms.

2. The apparatus for detecting changes in load applied thereto, according to claim 1, wherein:
   the elastic member (33) is rubber or elastomer fixed to a surface of the first plate, the surface being opposed to the side of the base member.

3. The apparatus for detecting changes in a load applied thereto, according to claim 2, further comprising:
   a transmission member which transmits the load change, received by the receiving member, applied to the elastic member.

4. The apparatus for detecting changes in a load applied thereto, according to claim 3, wherein:
   the transmission member is fixed to a section which includes the central axis of the elastic member.

5. The apparatus for detecting changes in a load applied thereto, according to claim 3, wherein:
   the transmission member is inserted through a hole section provided in a section which includes the central axis of the elastic member.

6. The apparatus for detecting changes in a load applied thereto, according to claim 3, further comprising:
   a second plate supporting a second surface of the elastic member on a side which opposes the side of the base member, and is fixed to the transmission member.

7. The apparatus for detecting changes in a load applied thereto, according to claim 6, wherein:
   the transmission member is provided with a section which is locked by a cover section; and
   the cover section is fixed to the base member, with the elastic member compressed toward the side of the base member, through the second plate fixed to the transmission member.

8. The apparatus for detecting changes in a load applied thereto, according to claim 1, further comprising:
   a buffer member provided at least at one of, a position between the heat flow sensors and the first plate, and a position between the heat flow sensors and the base member.

9. The apparatus for detecting changes in a load applied thereto, according to claim 1, wherein:
   the plurality of heat flow sensors are provided circumferentially around the central axis of the elastic member.

10. The apparatus for detecting changes in a load applied thereto, according to claim 9, wherein:
    the load change applied to the elastic member is detected by a detector which detects a size and direction of the load change, based on the output of the heat flow sensors.

11. The apparatus for detecting changes in a load applied thereto, according to claim 10, wherein:
    the plurality of heat flow sensors include a first heat flow sensor and a second heat flow sensor,
    the first heat flow sensor and the second heat flow sensor are disposed directly opposite to each other with the central axis of the elastic member provided therebetween, and
    the detector detects the size and the direction of the load change applied to the elastic member, based on an output corresponding to a difference between a thermal electromotive force of the first sensor and a thermal electromotive force of the second sensor.

12. The apparatus for detecting changes in a load applied thereto, according to claim 11, wherein:
    the plurality of sensors are provided with
    a third heat flow sensor, intersecting with a segment line joining the first heat flow sensor and the second heat flow sensor; and
    a fourth heat flow sensor disposed diametrically opposite the third heat flow sensor, with the central axis of the elastic member disposed between the diametrically opposed third heat flow sensor and fourth heat flow sensor, and
    the detector detects the size and the direction of the load change applied to the elastic member based on,
    a first signal which is the output corresponding to the difference between the thermal electromotive force of the first heat flow sensor and the thermal electromotive force of the second heat flow sensor, and
    a second signal which is the output corresponding to the difference between a thermal electromotive force of the third heat flow sensor and a thermal electromotive force of the fourth heat flow sensor.

13. The apparatus for detecting changes in a load applied thereto, according to claim 1, wherein:
    the heat flow sensor is formed in a circular shape around the central axis of the fixing member.

14. The apparatus for detecting changes in load applied thereto, according to claim 1, wherein:
the elastic member is a cantilever beam which extends from the lower plate to an exterior side thereof.

15. The apparatus for detecting changes in a load applied thereto, according to claim 2, further comprising:
a buffer member provided at least at one of, a position between the heat flow sensors and the first plate, and a position between the heat flow sensors and the base member.

16. The apparatus for detecting changes in a load applied thereto, according to claim 3, further comprising:
a buffer member provided at least at one of, a position between the heat flow sensors and the first plate, and a position between the heat flow sensors and the base member.

17. The apparatus for detecting changes in a load applied thereto, according to claim 2, wherein:
the plurality of heat flow sensors are provided circumferentially around the central axis of the elastic member.

18. The apparatus for detecting changes in a load applied thereto, according to claim 3, wherein:
the plurality of heat flow sensors are provided circumferentially around the central axis of the elastic member.

19. The apparatus for detecting changes in a load applied thereto, according to claim 2, wherein:
the heat flow sensor is formed in a circular shape around the central axis of the fixing member.

20. The apparatus for detecting changes in load applied thereto, according to claim 2, wherein:
the elastic member is a cantilever beam which extends from the lower plate to an exterior side thereof.

* * * * *